(12) United States Patent
Moyer et al.

(10) Patent No.: US 12,059,134 B2
(45) Date of Patent: Aug. 13, 2024

(54) INGESTIBLE DEVICE WITH MANIPULATION CAPABILITIES

(71) Applicant: Endiatx, Redwood City, CA (US)

(72) Inventors: Daniel V. Moyer, Redwood City, CA (US); Torrey P. Smith, Redwood City, CA (US); James G. Erd, Newark, CA (US); Daniel A. Luebke, San Mateo, CA (US); Benjamin J. Bonnes, Oakland, CA (US)

(73) Assignee: ENDIATX, INC., Hayward, CA (US)

( * ) Notice: Subject to any disclaimer, the term of this patent is extended or adjusted under 35 U.S.C. 154(b) by 513 days.

(21) Appl. No.: 16/915,922

(22) Filed: Jun. 29, 2020

(65) Prior Publication Data

US 2020/0405132 A1 Dec. 31, 2020

Related U.S. Application Data

(60) Provisional application No. 62/868,109, filed on Jun. 28, 2019.

(51) Int. Cl.
*A61B 10/04* (2006.01)
*A61B 1/00* (2006.01)
(Continued)

(52) U.S. Cl.
CPC .......... *A61B 10/04* (2013.01); *A61B 1/00006* (2013.01); *A61B 1/00009* (2013.01); *A61B 1/00016* (2013.01); *A61B 1/00032* (2013.01); *A61B 1/00036* (2013.01); *A61B 1/0011* (2013.01); *A61B 1/00156* (2013.01);
(Continued)

(58) Field of Classification Search
None
See application file for complete search history.

(56) References Cited

U.S. PATENT DOCUMENTS 1,748,345 A 2/1930 Hellmann
2,761,710 A 9/1956 Rudner
(Continued)

FOREIGN PATENT DOCUMENTS

CN 106462756 A 2/2017
IT 20080171 A1 3/2010
(Continued)

OTHER PUBLICATIONS

Notice of Allowance of U.S. Appl. No. 16/915,787, mailed Mar. 11, 2021, 12 pages.
(Continued)

*Primary Examiner* — John P Leubecker
*Assistant Examiner* — Jae Woo
(74) *Attorney, Agent, or Firm* — Perkins Coie LLP; Jordan Becker

(57) ABSTRACT

Introduced here is an ingestible device that can comprise a capsule, an intervention tool, and a processor configured to controllably employ the intervention tool to manipulate structures in a living body. The ingestible device may further comprise a camera that is configured to generate images of various in vivo environments as the ingestible device traverses the living body. These images may be wirelessly transmitted to an electronic device located outside of the living body to enable greater control over the intervention tool.

23 Claims, 33 Drawing Sheets

(51) Int. Cl.

| | |
|---|---|
| A61B 1/04 | (2006.01) |
| A61B 1/045 | (2006.01) |
| A61B 1/06 | (2006.01) |
| A61B 1/31 | (2006.01) |
| A61B 17/34 | (2006.01) |
| H01Q 7/00 | (2006.01) |
| H01Q 9/00 | (2006.01) |
| H04B 1/713 | (2011.01) |
| H04N 5/40 | (2006.01) |
| H04N 17/00 | (2006.01) |
| H04N 23/54 | (2023.01) |
| H04N 23/56 | (2023.01) |
| H04N 23/65 | (2023.01) |
| H04N 23/66 | (2023.01) |
| H04N 23/695 | (2023.01) |
| H04W 76/14 | (2018.01) |
| A61B 10/02 | (2006.01) |
| H04N 23/50 | (2023.01) |

(52) U.S. Cl.
CPC ............ *A61B 1/0016* (2013.01); *A61B 1/041* (2013.01); *A61B 1/045* (2013.01); *A61B 1/0661* (2013.01); *A61B 1/31* (2013.01); *A61B 17/3478* (2013.01); *A61B 17/3496* (2013.01); *H01Q 7/00* (2013.01); *H01Q 9/00* (2013.01); *H04B 1/713* (2013.01); *H04N 5/40* (2013.01); *H04N 17/002* (2013.01); *H04N 23/54* (2023.01); *H04N 23/56* (2023.01); *H04N 23/651* (2023.01); *H04N 23/66* (2023.01); *H04N 23/695* (2023.01); *H04W 76/14* (2018.02); *A61B 1/06* (2013.01); *A61B 2010/0208* (2013.01); *A61B 2010/045* (2013.01); *H04N 23/555* (2023.01)

(56) References Cited

U.S. PATENT DOCUMENTS

| | | | |
|---|---|---|---|
| 3,591,109 | A | 7/1971 | McLarty |
| 3,709,187 | A | 1/1973 | Marco et al. |
| 3,790,105 | A | 2/1974 | Fickman |
| 3,854,732 | A | 12/1974 | Franz et al. |
| 4,936,835 | A | 6/1990 | Haaga |
| 5,295,643 | A | 3/1994 | Ebbert et al. |
| 5,313,934 | A | 5/1994 | Wiita et al. |
| 5,393,197 | A | 2/1995 | Lemont et al. |
| 5,810,289 | A | 9/1998 | Sager |
| 5,993,378 | A * | 11/1999 | Lemelson ......... A61M 25/0069 |
| | | | 600/109 |
| 6,110,128 | A | 8/2000 | Andelin et al. |
| 6,240,312 | B1 | 5/2001 | Alfano et al. |
| 6,939,290 | B2 | 9/2005 | Iddan |
| 6,958,034 | B2 | 10/2005 | Iddan |
| 7,643,865 | B2 | 1/2010 | Iddan et al. |
| 7,647,090 | B1 | 1/2010 | Frisch et al. |
| 7,807,251 | B1 | 10/2010 | Wallach |
| 7,857,767 | B2 | 12/2010 | Ferren et al. |
| 7,998,060 | B2 | 8/2011 | Ferren et al. |
| 8,019,413 | B2 | 9/2011 | Ferren et al. |
| 8,038,600 | B2 | 10/2011 | Uchiyama et al. |
| 8,414,559 | B2 | 4/2013 | Gross |
| 8,439,851 | B2 | 5/2013 | Chiba et al. |
| 8,517,927 | B2 | 8/2013 | Asada et al. |
| 8,529,436 | B2 | 9/2013 | Jung et al. |
| 8,829,706 | B1 | 9/2014 | Sammy |
| 9,795,330 | B2 | 10/2017 | Pascal et al. |
| 2002/0120178 | A1 | 8/2002 | Tartaglia et al. |
| 2002/0198439 | A1 | 12/2002 | Mizuno |
| 2003/0019572 | A1 | 1/2003 | Low et al. |
| 2003/0167000 | A1 * | 9/2003 | Mullick ............... A61B 5/6882 |
| | | | 600/424 |
| 2003/0214579 | A1 * | 11/2003 | Iddan ..................... H04N 7/18 |
| | | | 348/81 |
| 2003/0214580 | A1 | 11/2003 | Iddan |
| 2004/0050394 | A1 * | 3/2004 | Jin ......................... A61B 34/73 |
| | | | 128/899 |
| 2004/0171914 | A1 | 9/2004 | Avni |
| 2005/0036059 | A1 | 2/2005 | Goldwasser |
| 2005/0124858 | A1 | 6/2005 | Matsuzawa et al. |
| 2006/0004276 | A1 | 1/2006 | Iddan et al. |
| 2006/0030754 | A1 | 2/2006 | Iddan |
| 2006/0078897 | A1 | 4/2006 | Wedinger et al. |
| 2006/0195015 | A1 * | 8/2006 | Mullick ............. A61B 1/00094 |
| | | | 600/102 |
| 2007/0250126 | A1 | 10/2007 | Maile et al. |
| 2008/0071139 | A1 | 3/2008 | Fujita |
| 2008/0114224 | A1 | 5/2008 | Bandy et al. |
| 2008/0262302 | A1 | 10/2008 | Nolan et al. |
| 2009/0099418 | A1 | 4/2009 | Kimoto |
| 2009/0253999 | A1 | 10/2009 | Aoki et al. |
| 2009/0312618 | A1 | 12/2009 | Hengerer et al. |
| 2009/0312787 | A1 * | 12/2009 | Chiba .................... A61B 5/073 |
| | | | 600/481 |
| 2010/0010330 | A1 | 1/2010 | Rankers et al. |
| 2010/0074778 | A1 | 3/2010 | Marcus |
| 2010/0158705 | A1 | 6/2010 | Guinard |
| 2010/0326703 | A1 | 12/2010 | Gilad et al. |
| 2011/0017612 | A1 | 1/2011 | Dijksman et al. |
| 2011/0034768 | A1 | 2/2011 | Ozaki et al. |
| 2011/0037268 | A1 | 2/2011 | Sammy |
| 2011/0065987 | A1 * | 3/2011 | Mullick ................. A61B 1/126 |
| | | | 600/109 |
| 2011/0166416 | A1 | 7/2011 | Katayama et al. |
| 2011/0213205 | A1 | 9/2011 | Uchiyama et al. |
| 2011/0282144 | A1 | 11/2011 | Gettman |
| 2012/0209074 | A1 | 8/2012 | Titus |
| 2012/0266116 | A1 | 10/2012 | Ding et al. |
| 2012/0289776 | A1 * | 11/2012 | Keast .................. A61B 17/0293 |
| | | | 600/114 |
| 2012/0292911 | A1 | 11/2012 | Bolin |
| 2013/0018224 | A1 | 1/2013 | Kim et al. |
| 2013/0310643 | A1 | 11/2013 | Gora et al. |
| 2016/0010498 | A1 | 1/2016 | Taylor |
| 2016/0141485 | A1 | 5/2016 | Lee |
| 2016/0345810 | A1 | 12/2016 | Hiraide |
| 2017/0119278 | A1 | 5/2017 | Hyde et al. |
| 2017/0296092 | A1 * | 10/2017 | Jones ...................... A61B 5/002 |
| 2017/0316133 | A1 | 11/2017 | Abramov |
| 2018/0312234 | A1 | 11/2018 | Garthwaite |
| 2018/0370609 | A1 | 12/2018 | Garthwaite |
| 2021/0178894 | A1 | 6/2021 | Umezawa |

FOREIGN PATENT DOCUMENTS

| | | |
|---|---|---|
| JP | 2015-0188614 | 11/2015 |
| JP | 6473266 B1 | 2/2019 |
| KR | 20-0446281 | 10/2009 |
| WO | 2020100321 A1 | 5/2020 |
| WO | WO-2020100321 A1 * | 5/2020 ......... A61B 1/00156 |

OTHER PUBLICATIONS

International Search Report and Written Opinion of the International Searching Authority dated Sep. 24, 2020, which is issued in corresponding International Application No. PCT/US20/40192.

Non-final Office Action mailed Aug. 5, 2022 for U.S. Appl. No. 16/915,735, 32 pages.

Examination Report for AU Patent Application No. 2020304682, mailed Sep. 15, 2022; 5 pages., Sep. 15, 2022.

Examination Report for AU Patent Application No. 2020302753, mailed Sep. 16, 2022; 4 pages., Sep. 16, 2022.

Notice of Allowance mailed Nov. 28, 2022 for U.S. Appl. No. 16/915,735, 15 pages., Nov. 28, 2022.

Non-Final Office Action mailed Jan. 25, 2021 for U.S. Appl. No. 16/915,787, filed Jun. 29, 2020, 16 pages., Jan. 25, 2021.

International Search Report and Written Opinion mailed Nov. 18, 2020 for International Application No. PCT/US20/40188 filed Jun. 29, 2020, 17 pages., Nov. 18, 2020.

(56) References Cited

OTHER PUBLICATIONS

Non-Final Office Action for U.S. Appl. No. 17/360,797 mailed Feb. 6, 2023, 24 pages.
Office Action for JP2021-577905 mailed Mar. 10, 2023, 5 pages., Feb. 10, 2023.
Office Action for JP2021-577984 mailed Feb. 10, 2023; 4 pages., Feb. 10, 2023.
Office Action for CA3144435 mailed Feb. 13, 2023, 2 pages., Feb. 13, 2023.
Office Action for CA3144331 mailed Feb. 9, 2023, 3 pages., Feb. 9, 2023.
Ciuti, Gastone, et al., "Capsule Endoscopy: From Current Achievements to Open Challenges", IEEE Reviews Inbiomedical Engineering, vol. 4, Oct. 10, 2011, pp. 59-72, Oct. 10, 2011.
De Falco, Iris, et al., "An Integrated System for Wireless Capsule Endoscopy in a Liquid-Distended Stomach", IEEE Transactions on Biomedical Engineering, vol. 61, No. 3, Mar. 31, 2014, pp. 794-804, Mar. 31, 2014.
Office Action received for Australian Patent Application No. 2020304682 mailed Apr. 2, 2023, 3 pages.
Tortora, G. et al., Propeller-Based wireless device for active capsular endoscopy in the gastric district, Minimally Invasive Therapy and Allied Technologies, 2009, pp. 280-290, Informa Healthcare, DOI: 10.1080/13645700903201167.
Carta, R. et al., Wireless powering for a self-propelled and steerable endoscopic capsule for stomach inspection, Biosensors and Bioelectronics, Sep. 4, 2009, pp. 845-851.
China National Intellectual Property Administration (CNIPA), Second Office Action, May 14, 2024, English summary appended.
European Patent Office (EPO), Article 94(3) EPC, May 15, 2024.

\* cited by examiner

1000

1001
Subject ingests an ingestible device

1002
Generate image data as the ingestible device travels through the living body

1003
Store the image data in a memory located in the ingestible device

1004
Cause wireless transmission of at least some of the image data to a receiver

1101
Insert propulsive device into a living body

1102
Receive first input indicative of an instruction to generate image data from a controller 1103
Cause an optical sensor to begin generating image data in response to the first input 1104
Cause wireless transmission of at least some of the image data to a receiver via an antenna 1105
Receive second input indicative of an instruction to move so that a given structure can be observed by the optical sensor 1106
Cause at least one propulsor to be driven in response to the second input

*FIGURE 11*

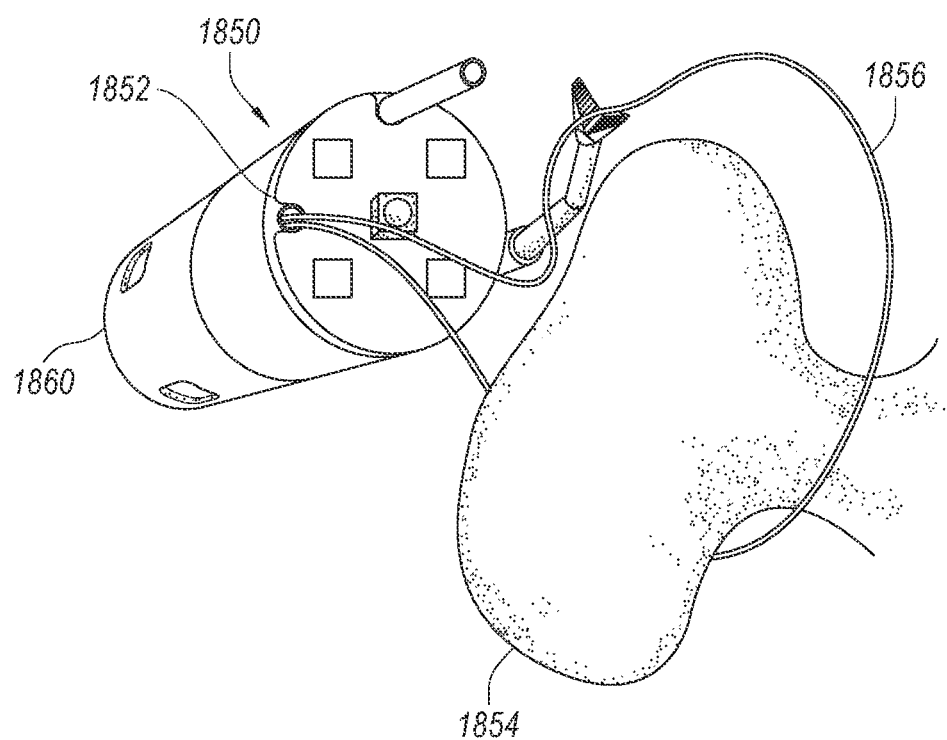
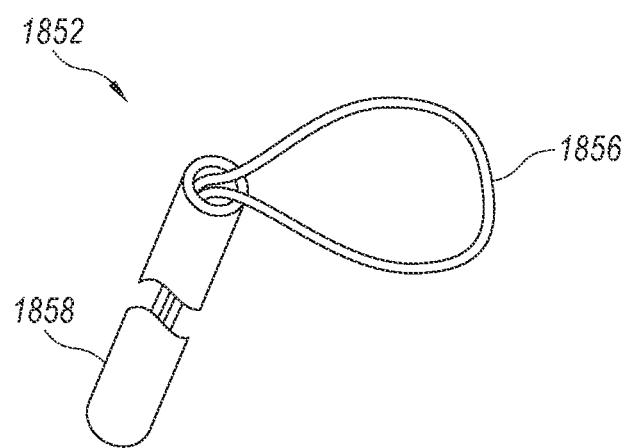
FIGURE 18B ated images of biological structures located inside of a living body and then transmit the images to an electronic device located outside of the living body.

INGESTIBLE DEVICE WITH MANIPULATION CAPABILITIES

CROSS-REFERENCE TO RELATED APPLICATIONS

This application claims the benefit of U.S. Provisional Patent Application No. 62/868,109, titled "Ingestible Device with Propulsion and Imaging Capabilities" and filed on Jun. 28, 2019, which is incorporated by reference herein in its entirety.

TECHNICAL FIELD

Various embodiments concern devices designed to generate images of biological structures located inside of a living body and then transmit the images to an electronic device located outside of the living body.

BACKGROUND

An endoscopy is a medical procedure during which structures within a living body are visually examined with a camera that is affixed to the end of a flexible tube. Alternatively, an optical fiber exposed near the end of the flexible tube may carry light reflected by the structures within the body to a camera located outside the living body. The flexible tube is used to position the camera or the optical fiber in a desired position. A medical professional can diagnose conditions that affect the living body by examining images generated by the camera. For example, during an upper endoscopy, the flexible tube is inserted through the mouth or nose so that the medical professional can examine the esophagus, stomach, or upper part of the small intestine (also referred to as the "duodenum"). During a lower endoscopy (also referred to as a "colonoscopy"), the flexible tube is inserted through the rectum so that the medical professional can examine the large intestine (also referred to as the "colon").

Advances have been made in the quality, reliability, and safety of endoscopies. For instance, improvements in camera resolution have allowed medical professionals to provide more informed (and thus more accurate) opinions. Endoscopies are invasive procedures, however, and therefore have several potential complications. Patients may suffer infection, unexpected reactions to sedation (including death), bleeding (e.g., due to the removal of tissue for testing as part of a biopsy test), or tearing of tissue due to the friction of advancing the flexible tube through tortuosity, especially in cancer patients where chemotherapy drugs have weakened the tissues of the gastrointestinal (GI) tract or in pediatric patients whose anatomy is more fragile and/or physically smaller.

Moreover, endoscopies can be time-consuming procedures that require expensive hospital resources. For example, a patient may be instructed to prepare for an endoscopy while at home, travel to a medical setting, and then remain in the medical setting until sufficient recovery has occurred. This experience can take 8-12 hours despite the endoscopy itself lasting only 15-30 minutes. Recovery time associated with sedation that is spent in a medical setting, such as a hospital or a clinic, may be a significant contributor to the overall cost of the procedure.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 10 depicts a flow diagram of a process for monitoring an in vivo environment using a device designed for ingestion by a living body.

FIG. 11 depicts a flow diagram of a process for controlling a propulsive ingestible device that has an optical sensor as it travels through a living body.

FIG. 18B is a perspective of another ingestible device with an intervention component capable of excising a polyp.

DETAILED DESCRIPTION

Figure 1:
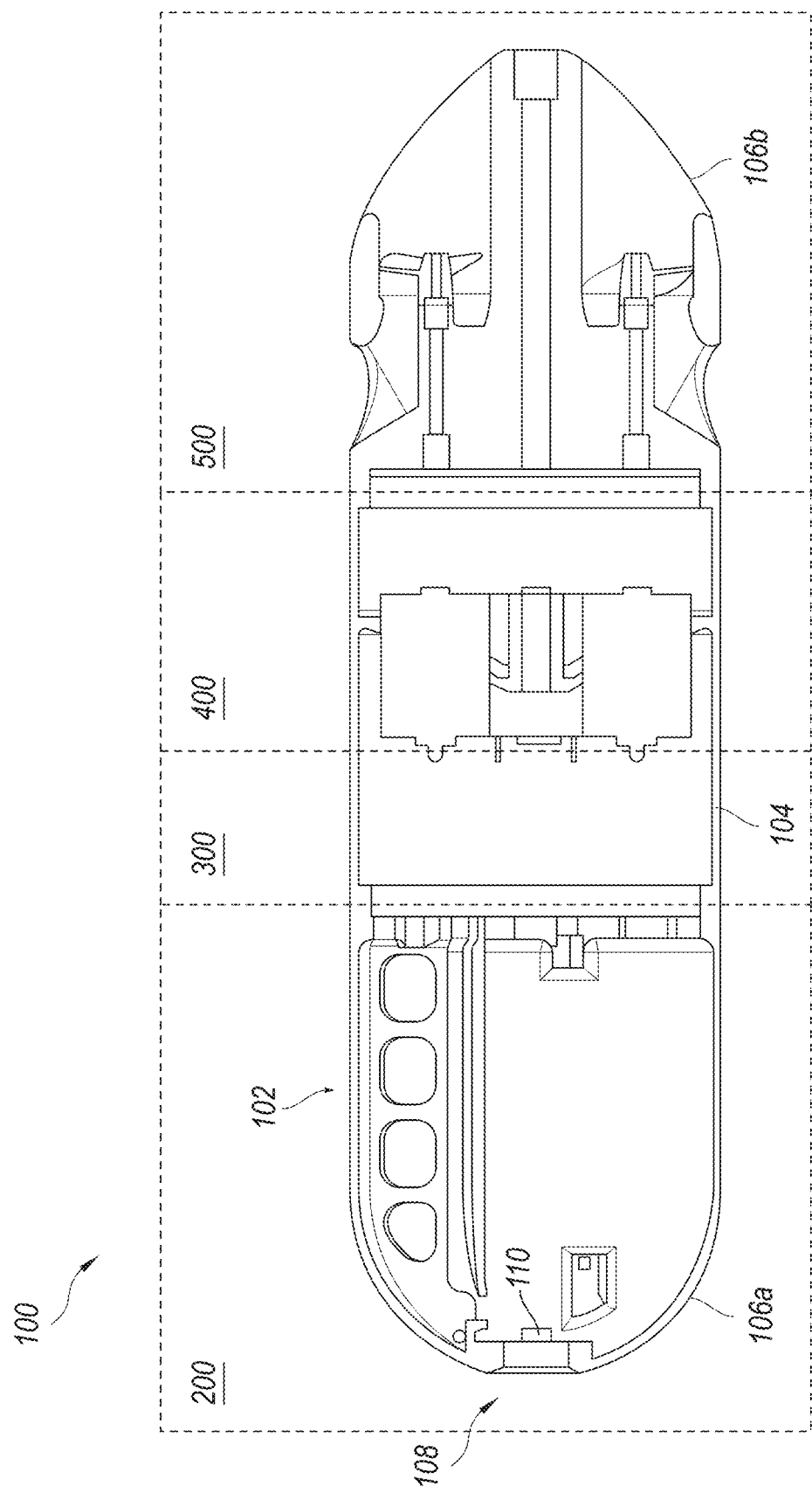
FIG. 1 includes a cross-sectional view of an example of a propulsive ingestible device designed to monitor in vivo environments as it travels through a living body, such as a human body or an animal body, under its own power.

Contemporary research has begun exploring how to monitor in vivo environments in a more effective manner. For example, several entities have developed cameras capable of capturing images of the digestive tract. Generally, these cameras are placed within vitamin-size capsules that can be swallowed by patients. The camera can generate hundreds or thousands of images as the capsule travels through the digestive tract, and these images can be wirelessly transmitted to an electronic device carried by the patient. This procedure is referred to as "capsule endoscopy."

Capsule endoscopy allows medical professionals to observe in vivo environments, such as the small intestine, that cannot easily be reached with conventional endoscopes. However, capsule endoscopy remains a relatively uncommon procedure. One reason for this is the lack of control over the camera following ingestion of the capsule. Areas of interest can be missed by the camera due to the orientation of the capsule as it naturally travels through the digestive tract. Another reason is that the devices used for capsule endoscopy can take several hours to reach the target anatomy and then several more hours to record imagery. Then, the patient may need to return to a medical setting (e.g., a hospital or clinic) to deliver the recorded imagery.

Introduced here, therefore, is a propulsive ingestible device (also referred to as a "pill" or a "pillbot") comprising a capsule (also referred to as an "enclosure"), a camera, an antenna, and one or more propulsion components and propulsion control elements. Because the ingestible device is designed to propel itself through a living body, the ingestible device may be referred to as a "propulsive device."

The camera can generate images as the ingestible device traverses the gastrointestinal tract. The camera may be designed to capture images at a variety of frame rates, for example 2, 6, or 15 frames per second (fps). In some embodiments, the camera may capture more than 15 fps. The frame rate may vary based on the speed at which the ingestible device is traveling. For instance, the ingestible device may be designed to increase the frame rate as the speed increases. Images generated by the camera are forwarded to the antenna for transmission to an electronic device located outside of the living body. More specifically, a processor may transmit the images to a transceiver responsible for modulating the images onto the antenna for transmission to the electronic device. In some embodiments, the images are transmitted to the electronic device in real time so that a medical professional can take appropriate action(s) based on the content of the images. For example, the medical professional may discover an area of interest that requires further examination upon reviewing the images. In such a scenario, the propulsion component(s) can orient the propulsive ingestible device so that the camera is focused on the area of interest. Such action may enable the ingestible device to gather additional data (e.g., in the form of images, biological measurements, etc.) regarding the area of interest.

The medical professional may be a general practitioner, specialist (e.g., a surgeon or a gastroenterologist), nurse, or technologist who is responsible for managing the ingestible device as it travels through the living body. Unlike conventional endoscopies, however, the medical professional need not be located in close proximity to the patient (also referred to as a "subject") undergoing examination. For example, the medical professional may examine images generated by the camera on an electronic device located in a remote hospital while the patient lies in another environment, such as a home, battlefield, etc. In this way, capabilities of a traditional GI department may be extended using the technologies described herein.

In some embodiments, the ingestible device includes at least one intervention component (also referred to as an "intervention device," "intervention mechanism," "implement," or "tool") that can be used to manipulate structures within the body. These intervention component(s) may allow advanced diagnostics and treatments to be performed beyond analysis of images generated by the camera. As further discussed below, an ingestible device may include intervention components that can be used to sample fluid and/or tissue, deliver medication, mark anatomical sites for subsequent reacquisition, cauterize tissue, and other procedures. At a high level, the inclusion of intervention component(s) enables an ingestible device to perform diagnostics and/or interventions that have traditionally been available to medical professionals only through use of conventional endoscopes.

Embodiments may be described with reference to particular capsule shapes, propulsion components, sensors, networks, etc. However, those skilled in the art will recognize that the features of these embodiments are equally applicable to other capsule shapes, propulsion components, sensors, networks, etc. For example, although a feature may be described in the context of an ingestible sensor that has multiple propellers arranged in a cross-type configuration, the feature may be embodied in an ingestible sensor having another type of propulsor, or propellers in a different arrangement, or a combination of these variations.

Ingestible Device Overview

FIG. 1 includes a cross-sectional view of an example of an ingestible device 100 designed to monitor in vivo environments as it travels through a living body, such as a human body or an animal body. Note that FIG. 1 and other illustrations in this document are not drawn to scale and are shown significantly enlarged for greater clarity. Because the ingestible device 100 can be designed to propel itself through a living body, the ingestible device 100 may be referred to as a "propulsive device." The ingestible device 100 includes a capsule 102 with a cylindrical body 104 and hydrodynamic, atraumatically shaped ends 106a-b. One example of a hydrodynamic, atraumatically shaped end is a rounded shape that does not cause damage upon contacting living tissue, such as the roughly hemispherical ends shown in FIG. 1. This geometric shape may be referred to as a "spherocylinder." While the ingestible device 100 shown in FIG. 1 has roughly hemispherical ends, other hydrodynamically-shaped ends may be included in other embodiments. For example, at least one end of the capsule 102 may be a dome with a flat portion through which light can be guided toward an optical sensor. As another example, at least one end of the capsule 102 may be a truncated cone. At least one end of the capsule 102 may also feature fillets that leave flat or minimally curved surfaces along those end(s). The cylindrical body 104 and hemispherical ends 106a-b may collectively be referred to as the "structural components" of the capsule 102. To avoid contamination of an internal cavity defined by the cylindrical body 104 and/or hemispherical ends 106a-b, the structural components may be hermetically sealed to one another.

In some embodiments, these structural components comprise the same material. For example, the structural components may comprise plastic (e.g., polyethylene (PE), polyvinyl chloride (PVC), polyetheretherketone (PEEK), acrylonitrile butadiene styrene (ABS), polycarbonate, nylon, etc.), stainless steel, titanium-based alloy, or another biocompatible material. The term "biocompatible," as used herein, means not harmful to living tissue. Biocompatible polymers may be three-dimensional (3D) printed, machined, sintered, injection molded, or otherwise formed around components of the ingestible device 100. In other embodiments, these structural components comprise different materials. For example, the hemispherical end 106a in which an optical sensor 110 is mounted may be comprised of a transparent plastic, while the other hemispherical end 106b and cylindrical body 104 may be comprised of a polymer or metallic alloy. Moreover, these structural components may include a coating that inhibits exposure of the structural components themselves to the in vivo environment. For example, these structural components may be coated with silicone rubber, diamond-like carbon, Teflon, or some other biocompatible, hydrophobic, or hydrophilic coating that aids in safety, durability, or operational efficiency of the ingestible device 100. Additionally or alternatively, these structural components may be coated with an antibacterial material, such as antibiotic-loaded polymethyl methacrylate (PMMA).

As shown in FIG. 1, at least one hemispherical end 106a can include an opening 108 through which the field of view of an optical sensor 110 extends. In some embodiments, the opening 108 is filled with a transparent material, such as glass or plastic. Alternatively, the optical sensor 110 may be positioned such that its outermost lens substantially aligns with the exterior surface of the hemispherical end 106a, or the optical sensor 110 may be positioned such that the focal length of the lens is similar to the radius of the hemispherical end 106a such that focus is ensured for any anatomy that directly contacts the ingestible device 100. While the hemispherical end 106a shown in FIG. 1 includes a single opening, other embodiments of the hemispherical end 106a may include multiple openings (e.g., for multiple optical sensors, biometric sensors, or combinations thereof). In some embodiments, the hemispherical end 106a is entirely comprised of a transparent material. In such embodiments, the hemispherical end 106a may not include a dedicated opening for the optical sensor 110 since the optical sensor 110 can generate image data using electromagnetic radiation that has penetrated the transparent material. The hemispherical end 106a may include surface features that diffuse or direct illumination leaving the ingestible device 100. Moreover, a portion of the hemispherical end 106a may be rendered substantially opaque to inhibit or eliminate interval reflections of light that may interfere with the optical sensor 110.

Due to the convenience in manufacturing, the opening 108 will often be circular. However, the opening 108 could have other forms. For example, in some embodiments the opening 108 is rectangular, while in other embodiments the opening 108 has a rectangular portion with circular endpoints. These circular endpoints may be oriented on opposing sides of the hemispherical end 106a so that optical sensors positioned beneath the circular endpoints can observe the in vivo environment along both sides of the propulsive ingestible device 100.

In various embodiments, the capsule 102 may have any of a variety of different sizes, such as any of those listed in Table I.

TABLE I

Example sizes of capsules.

| | Size | | | | | | |
|---|---|---|---|---|---|---|---|
| | 000 | 00 | 0 | 1 | 2 | 3 | 4 |
| Internal Cavity Capacity (ml) | 1.37 | 0.91 | 0.68 | 0.50 | 0.37 | 0.30 | 0.21 |
| Length (mm) | 35 | 30 | 29 | 26.5 | 24 | 21.5 | 19.5 |
| Diameter (mm) | 15 | 13.5 | 11 | 7 | 6.5 | 6 | 5.5 |

As shown in FIG. 1, the ingestible device 100 can include four sections having different responsibilities: a payload section 200, a power section 300, a drive section 400, and a propulsion section 500. Each of these sections is described in greater detail below with respect to FIGS. 2, 3, 4, and 5, respectively. While these sections are illustrated as being distinct from one another, the component(s) associated with each section may not necessarily be located within the corresponding box shown in FIG. 1. For example, the power section 300 may include a power distribution unit that extends into the payload section 200, drive section 400, and/or propulsion section 500 to deliver power to component(s) in those sections.

Figure 2B:
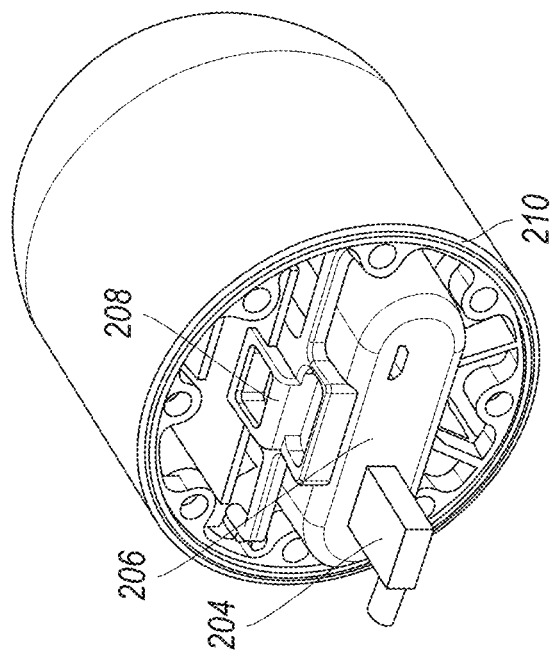
FIG. 2B includes a rear perspective view of the payload section of the ingestible device of FIG. 2A.
Figure 2A:
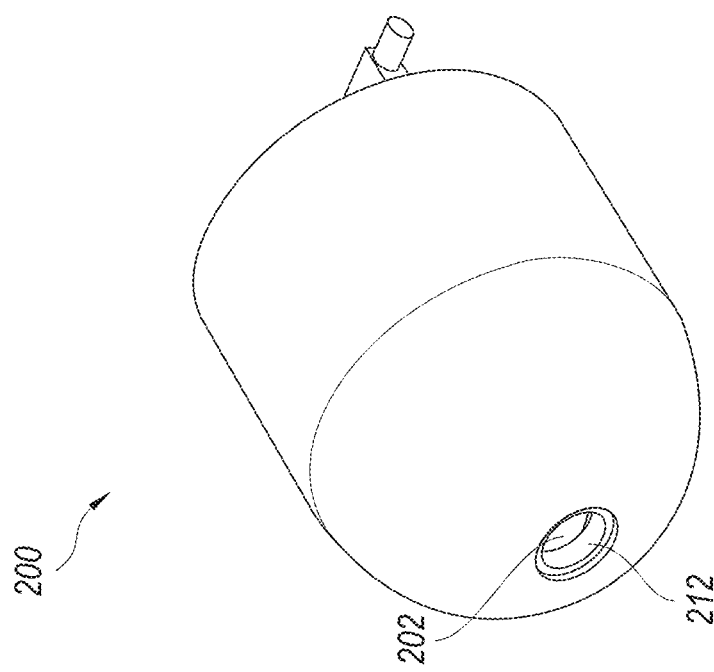
FIG. 2A includes a front perspective view of a payload section of an ingestible device.

FIG. 2A includes a front perspective view of the payload section 200 of the ingestible device, while FIG. 2B includes a rear perspective view of the payload section 200 of the ingestible device. The payload section 200 can include an optical sensor 202, a power and data bus 204, a control unit 206, a manipulator controller 208, a hermetic seal 210, and an illumination source 212. Embodiments of the ingestible device can include some or all of these components, as well as other components not shown here. For example, if the ingestible device has been designed solely for imaging, then the payload section 200 may not include a manipulator controller 208 since no manipulation will be performed. Embodiments of ingestible devices having intervention component(s) that are controlled by a manipulator controller are further discussed below with reference to FIGS. 13-26.

As the ingestible device traverses the gastrointestinal tract, the optical sensor 202 can generate image data based on electromagnetic radiation reflected by structures located in the gastrointestinal tract. For example, if the optical sensor 202 is a camera, then images or video may be captured as the ingestible device travels through the body. Another example of an optical sensor 202 is an infrared sensor. Other embodiments of the ingestible device may include an acoustic sensor, such as an ultrasonic sonic, instead of, or in addition to the optical sensor 202. Thus, the ingestible device may include one or more sensors configured to generate image data based on energy reflected by structured in the body. An illumination source 212 (also referred to as a "light source") housed in the ingestible device will typically be responsible for generating the electromagnetic radiation. An example of an illumination source 212 is a light-emitting diode (LED). Here, the illumination source 212 is arranged so that the electromagnetic radiation is emitted through the same aperture in the capsule through which the reflected electromagnetic radiation is received. In other embodiments, the illumination source 212 is arranged so that the electromagnetic radiation is emitted through a first aperture in the capsule while the reflected electromagnetic radiation is received through a second aperture in the capsule.

Some embodiments of the propulsive ingestible device include multiple optical sensors 202. For example, an ingestible device may include a camera equipped with a charge-coupled device (CCD) or a complementary metal-oxide-semiconductor (CMOS) sensor assembly capable of detecting electromagnetic radiation in the visible range and an infrared sensor capable of detecting electromagnetic radiation in the infrared range. These optical sensors can generate distinct sets of data that collectively provide meaningful information that may be useful in rendering diagnoses, as well as assisting with spatial positioning. Here, for instance, the infrared sensor may be able to measure the heat emitted by objects that are included in the colored images captured by the camera.

The power and data bus 204 (also referred to as a "bus" or "bus connector") may be responsible for distributing data and/or power to various components in the propulsive ingestible device. For example, the bus 204 may forward image data generated by the optical sensor 202 to the control unit 206, and the control unit 206 may forward the image data to a transceiver configured to modulate the data onto an antenna for transmission to a receiver located outside of the body. As further described below, the receiver may be part of an electronic device on which an individual can view images corresponding to the image data, control the ingestible device, etc. The bus 204 may include cables, connectors, wireless chipsets, processors, etc. In some embodiments, the bus 204 manages data and power on separate channels. For example, the bus 204 may manage data using a first set of cables and power using a second set of cables. In other embodiments, the bus 204 manages data and power on a single channel (e.g., with components capable of simultaneously transferring data and power).

The control unit 206 may be responsible for managing other components in the propulsive ingestible device. For example, the control unit 206 may be responsible for parsing inputs received by the antenna and then providing appropriate instructions to other components in the propulsive ingestible device. As further described below, an individual may provide the input using a controller device (or simply "controller") located outside of the body. The input may be representative of a request to begin generating image data using the optical sensor 202, begin transmitting image data using the antenna, cease generating image data using the optical sensor 202, cease transmitting image data using the antenna, or move the propulsive ingestible device to a desired location. The control unit 206 may include a central processing unit (CPU), graphics processing unit (GPU), application-specific integrated circuit (ASIC), field-programmable gate array (FPGA), microcontroller, logic assembly, or any combination of other similar processing units.

In some embodiments, the propulsive ingestible device is designed to manipulate in vivo environments in some manner. In such embodiments, the payload section 200 could include an intervention component such as a biopsy appendage, needle, cutting mechanism (e.g., $CO_2$ laser, argon laser, neodymium-doped yttrium aluminum garnet (Nd:YAG) laser, rotating cutting element, scissors, forceps, or dissector), pushing mechanism, grasping mechanisms (e.g., polypectomy implement), cauterization mechanism (e.g., ohmic cauterizer or radio-frequency (RF) cauterizer), or delivery mechanism (e.g., syringe, material impregnated with medication, or structure that encapsulate medications in their closed state). The manipulator controller 208 can control these intervention components. For example, the manipulator controller 208 may control a biopsy appendage that extends through the capsule to collect tissue based on instructions received from the control unit 206. More specifically, the manipulator controller 208 may extend the biopsy appendage through an aperture in the capture to collect a sample of tissue and then retract the biopsy appendage into the capsule through the aperture.

To prevent fluids from entering the capsule, the payload section 200 and power section 300 may be hermetically sealed to one another. Accordingly, a hermetic seal 210 may be secured along the interface between the payload section 200 and power section 300. The hermetic seal 210 may be comprised of epoxy resin, metal, glass, plastic(s), rubber(s), ceramic(s), glue or another sealing material. One factor in determining whether the material(s) used to form the hermetic seal 210 are appropriate is whether the surface energy of those material(s) is similar to the surface energy of the substrate to which the hermetic seal 210 is bound. Accordingly, the composition of the hermetic seal 210 may depend on the composition of the structural components of the capsule. For example, if the structural components of the capsule comprise stainless steel, then the hermetic seal 210 may be comprised of an epoxy resin having metal (e.g., stainless steel) particles suspended therein. Alternatively, the hermetic seal 210 may be formed using a flexible gasket, adhesive film, weld, seal, etc.

Figure 3:
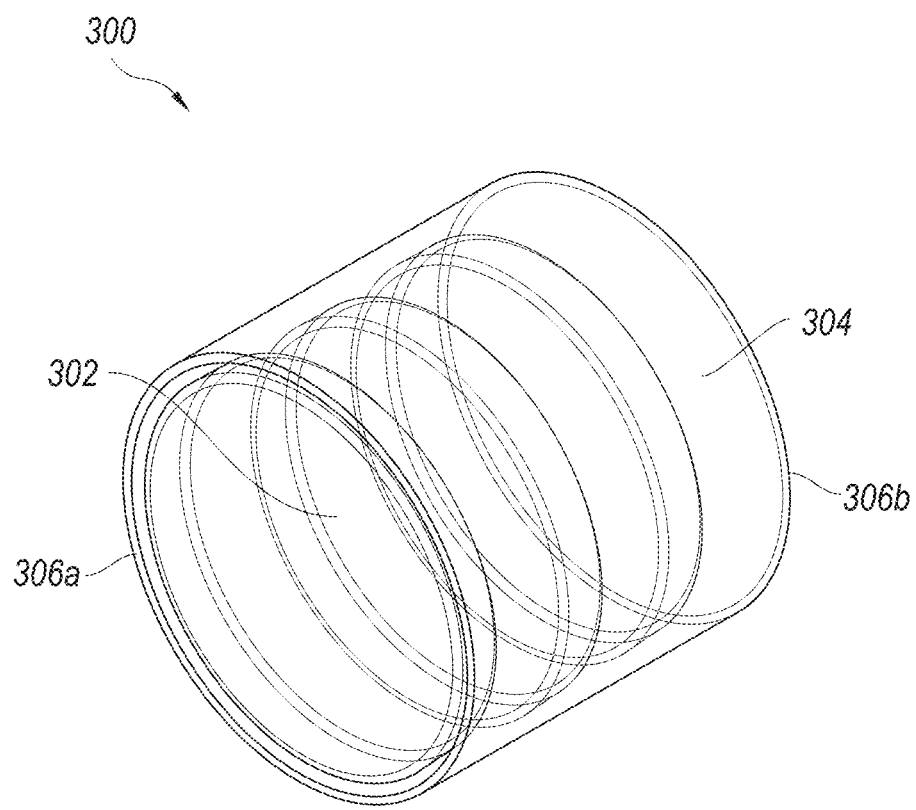
FIG. 3 includes a perspective view of a power section of an ingestible device.

FIG. 3 includes a perspective view of the power section 300 of the ingestible device. The power section 300 can include a power component 302, a power distribution unit 304, and a hermetic seal 306a-b secured along each end. The hermetic seals 306a-b may be substantially similar to the hermetic seal 210 secured to the payload section 200 as described with respect to FIG. 2. Moreover, the hermetic seal 210 secured to the lower end of the payload section 200 may be the same seal as the hermetic seal 306a secured to the upper end of the power section 300. Thus, a single hermetic seal may join the payload section 200 and power section 300.

The power component 302 (also referred to as an "energy storage component") can be configured to supply power to other components of the propulsive ingestible device, such as any optical sensor(s), biometric sensor(s), processor(s), communication components (e.g., transmitters, receivers, transceivers, and antennas), and any other components requiring power. For example, the power component 302 may be responsible for providing power needed by an optical sensor (e.g., optical sensor 202 of FIG. 2) to generate image data. As another example, the power component 302 may be responsible for generating the driving energy to be applied to an antenna to cause wireless transmission of the image data to a receiver located outside of the body.

The power component 302 could be, for example, a silver-oxide battery, nickel-cadmium battery, lithium battery (e.g., with liquid cathode cells, solid cathode cells, or solid electrolyte cells), capacitor, fuel cell, piezoelectric component, or another energy-capture and/or -storage device. In some embodiments, the power component 302 includes one or more battery plates that are exposed to the fluid(s) through which the ingestible device travels. In such embodiments, the power component 302 can be designed to run on a fluid (e.g., a bodily fluid such as stomach acid) that is readily accessible within the in vivo environment for which the ingestible device is designed. Normally, a battery operates by shuttling ions with a positive charge from one place to another through a solution called an electrolyte that has positively- and negatively-charged particles. In the case of exposed battery plates, however, a pair of metal electrodes can be secured to the exterior surface of the ingestible device. One metal electrode (e.g., comprised of zinc) can emit ions into the fluid, which acts as the electrolyte by carrying a small electric current to the other metal electrode (e.g., comprised of copper).

In some embodiments, the power component 302 is designed such that it can wirelessly receive power from a source located outside of the body. In such embodiments, the source can generate a time-varying electromagnetic field that transmits power to the power component 302. The power component 302 can extract power from the electromagnetic field and then supply the power to the other components in the ingestible device as necessary. The power may be received using either the same antenna as is used for data transmission or using a different antenna, inductively coupled coil, or capacitively coupled structure. The source could be the controller used for controlling the ingestible device, the electronic device used for reviewing image data, or some other electronic device (e.g., a mobile phone or a wireless charger belonging to the patient). Alternatively, the wireless power source may be included in an article, such as a belt or band, that can be worn such that the wireless power source is located near the ingestible device as it travels through the living body. Such a wearable article may include a battery pack that is integrated within the article itself or attached to the patient. Moreover, such a wearable article may include one or more antennas for data transmission.

The power component 302 may be designed to fit in a particular segment of the ingestible device. Here, for example, the power component 302 has a button cell form that permits the power component 302 to be secured within the cylindrical body of the capsule. However, other embodiments of the power component 302 may be designed to fit within a hemispherical end of the capsule or another area within the capsule.

As noted above, the power distribution unit 304 may be responsible for distributing power stored in the power component 302 to other components in the ingestible device. Accordingly, component(s) of the power distribution unit 304 may extend into the payload section 200, drive section 400, and/or propulsion section 500. For example, the power distribution unit 304 may include cables that are connected to the optical sensor, bus connector, control unit, control sensors, and/or manipulator controller that may be located in the payload section 200. The power distribution unit 304 may also include component(s) for regulating, stabilizing, or modifying the power to be distributed. Examples of such components include voltage regulators, converters (e.g., DC-to-DC converters), metal-oxide-semiconductor field-effect transistors (MOSFETs), capacitors, transformers, resistors, or inductors.

Figure 4:
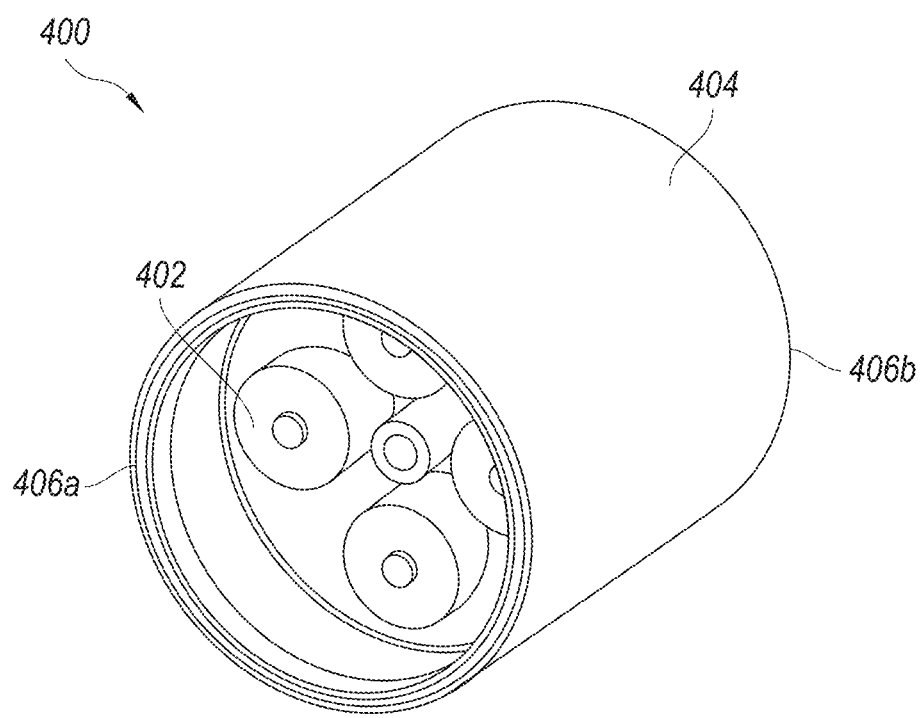
FIG. 4 includes a perspective view of a drive section of an ingestible device.

FIG. 4 includes a perspective view of the drive section 400 of the ingestible device. The drive section 400 can include energy-to-movement converter(s) 402, heat transfer component(s) 404, and a hermetic seal 406a-b secured along each end. The hermetic seals 406a-b may be the same as or substantially similar to the hermetic seal 210 secured to the payload section 200 as described with respect to FIG. 2. Moreover, the hermetic seal 306b secured to the lower end of the power section 300 may be the same seal as the hermetic seal 406a secured to the upper end of the drive section 400. Thus, a single hermetic seal may join the power section 300 and drive section 400.

Upon receiving power from a power distribution unit (e.g., the power distribution unit 304 of FIG. 3), the mechanical power converter(s) 402 can drive another component of the ingestible device. Here, for instance, the drive section 400 includes multiple motors, and each motor may be responsible for driving a different propulsor. Examples of motor(s) 402 include DC or AC electric motors, drivers comprised of a shape-memory alloy, electromagnets, shafts, piezoelectric components, etc. The propulsor may be connected to the motor by one or more shafts, gears, levers, bearings, etc.

Components in the ingestible device may produce heat that should be dissipated to avoid causing damage within the body. For example, components such as energy-to-movement converters and motor housings may generate heat if the propulsor(s) are driven for an extended period of time. Accordingly, these components may include or be connected to heat transfer component(s) 404 that are able to assist in dissipating this heat. In some embodiments, the heat transfer component(s) 404 discharge the heat directly into the fluid (e.g., water, bile, stomach acid, and mixtures thereof) surrounding the ingestible device. For example, the motor housings may be comprised of a material (e.g., stainless steel) having acceptable thermal conductivity to promote dissipation of heat. In other embodiments, the heat transfer component(s) 404 discharge the heat into the capsule. When heat is discharged into the capsule, the heat may naturally transfer into the fluid surrounding the ingestible device through conduction and convection.

Figure 5B:
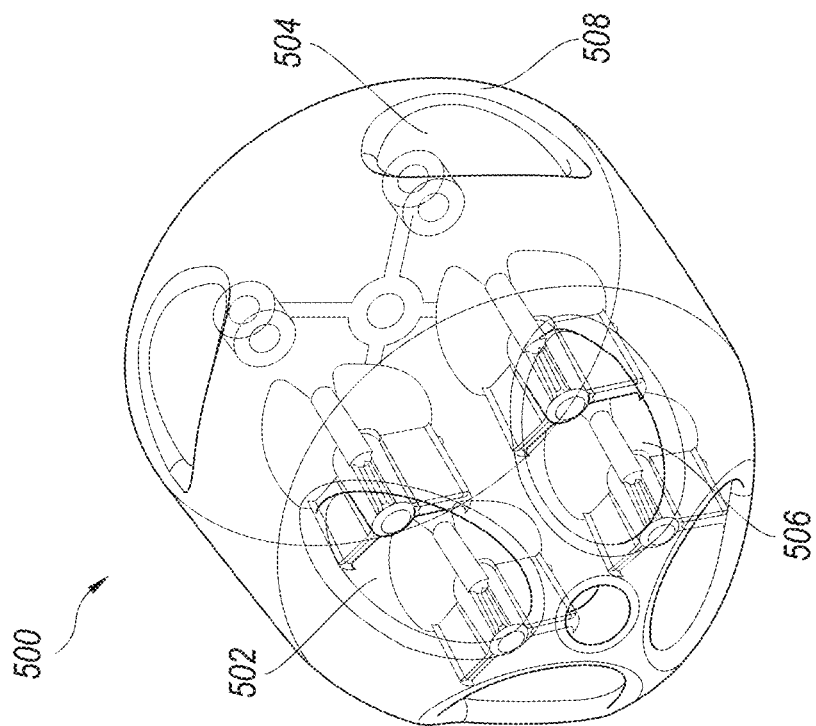
FIG. 5B includes a transparent perspective view of the propulsion section of the ingestible device of FIG. 5A.
Figure 5A:
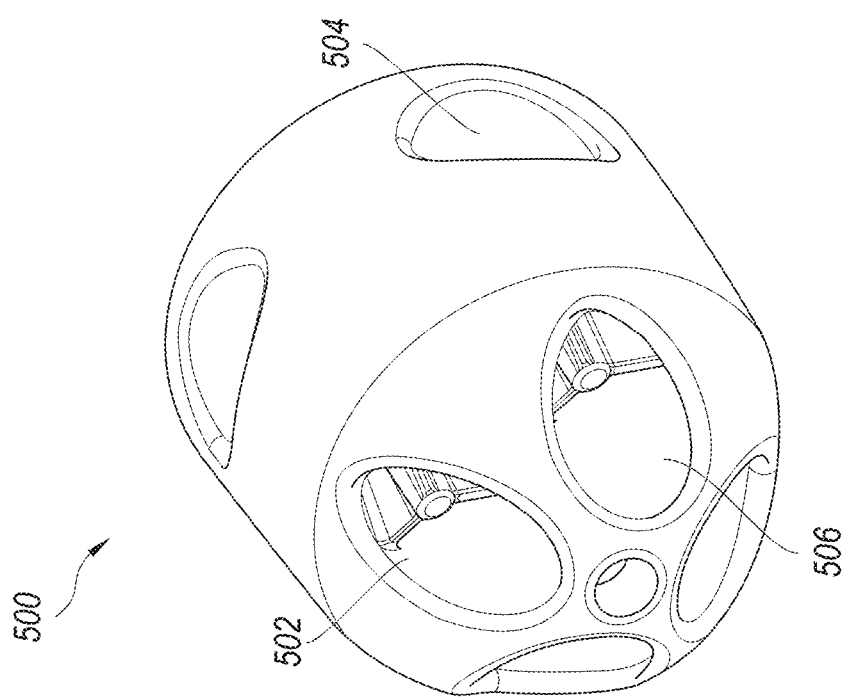
FIG. 5A includes a perspective view of a propulsion section of an ingestible device.

FIG. 5A includes a perspective view of the propulsion section 500 of the ingestible device, while FIG. 5B includes a transparent perspective view of the propulsion section 500 of the ingestible device. The propulsion section 500 can include one or more propulsors 502, one or more intakes 504, and a hermetic seal 508 secured along its upper end. The hermetic seal 508 may be substantially similar to the hermetic seal 210 secured to the payload section 200 as described with respect to FIG. 2. Moreover, the hermetic seal 508 may be the same seal as the hermetic seal 406b secured to the lower end of the drive section 400. Thus, a single hermetic seal may join the drive section 400 and propulsion section 500.

As noted above, the ingestible device may include one or more propulsion components (also referred to as "propulsion systems" or "thrust components"). Each propulsion component can include a propulsor configured to generate a propulsive force for moving the ingestible device and an energy-to-movement converter configured to supply motive power to the propulsor. Here, for example, the propulsion section 500 includes four rotors 502 that are driven by four motors located in the drive section 400. In some embodiments, each propulsor is driven by a different mechanical power converter. In other embodiments, multiple propulsors may be driven by a single energy-to-movement converter. For example, a single motor may be responsible for supplying motive power to multiple propulsors, though the speed of each propulsor may be varied through a mechanical connection (e.g., a clutch system or a gear system).

As further described below, multiple propulsors 502 can be arranged to facilitate movement along different axes. In FIGS. 5A-B, for example, four propulsors 502 are arranged radially about a central axis 516 defined through the capsule in a cross-type configuration. More specifically, these propulsors 502 are disposed at locations radially offset from the central axis and at different angular offsets about the central axis. By independently driving these propulsors 502, movement can be achieved in any direction or orientation, in a fashion similar to a quadcopter. Accordingly, the ingestible device may be commanded to move forward and backward at different speeds. Moreover, the ingestible device may be commanded to change its orientation through rotation about three mutually perpendicular axes. These changes in orientation and forward/backward motions can be converted into variations in yaw (normal axis), pitch (transverse axis), and roll (longitudinal axis), and therefore movement to any location can be represented in three-dimensional space.

In FIGS. 5A-B, the propulsors 502 are rotors capable of drawing fluid through intakes 504 formed in the capsule. The term "rotor," as used herein, refers to a component that is capable of rotating to create propulsive force. An example of a rotor is a propeller. However, other propulsors could be used instead of, or in addition to, the rotors. Examples of propulsion components include helicoids, fins, lash-like appendages (also referred to as "flagellum"), undulating mechanisms, etc. Moreover, propulsion components could be arranged along the cylindrical body of the capsule instead of, or in addition to, in the hemispherical end of the capsule. For example, an ingestible device may include oscillating fins arranged along opposing sides of the cylindrical body of the capsule. These oscillating fins may be used in conjunction with propeller(s), helicoid(s), or lash-like appendage(s) located in the hemispherical end of the capsule to provide greater control over the movement of the ingestible device.

As shown in FIGS. 5A-B, the capsule may include one or more channels through which fluid can be drawn by the propulsion(s) 502. Each channel includes an inlet 504 through which fluid can be drawn and an outlet 506 through which the fluid is discharged. Examples of inlets 504 include ducts, lumens, vanes, tubes, etc. While the embodiment shown in FIG. 5 includes an identical number of propulsors 502 and inlets 504, that need not always be the case. For example, a propeller mounted in the hemispherical end of the capsule may be able to draw fluid through one or more inlets to prevent moving components, such as the propulsor(s) 502, from touching living tissue. Rotational propeller efficiency may be optimized with fixed stator vanes so as to control swirl, increase velocity, and increase controllability, as further discussed below with respect to FIGS. 5C-D. In some embodiments, coaxial contra-rotating propellers may be used to obviate fixed stator vanes altogether. Propeller and vane blade count and geometry may be tuned to optimize clearing of bubbles and debris as a function of diameter, speed, and fluid properties.

In some embodiments, a filter is placed in at least one of the channels defined through the capsule. For example, a filter may be secured in each channel defined through the capsule. Filters may be necessary to ensure that objects suspended in the fluid drawn through the inlets 504 that exceed a particular size are removed. For example, if the ingestible device is designed for use within the gastrointestinal tract, the filter(s) may be designed to prevent solid particulates such as food particles from contacting the propulsor(s) 502.

Another issue is that propulsors tend to impart rotational motion on (or "stir") the fluid rather than create thrust unless designed properly. This problem can be addressed by adding one or more stator vanes (also referred to as "stator blades") to each flow channel. The terms "stator vane" and "stator blade" refer to a fixed blade positioned within the flow channel through which fluid is drawn and then ejected by a propeller. FIG. 5C illustrates how propulsor(s) 502 may be arranged adjacent to stator vanes 514 in a distal element 512 of the ingestible device of FIGS. 5A-B. These stator vanes 514 may serve to straighten the fluid flow, reduce the stirring effect, and increase thrust and thrust consistency. As shown in FIG. 5C, each propulsor 402 may be connected to a separate motor housing 510 in which the motor responsible for driving the propulsor is located. The propulsors 502 (and thus the motor housings 510) may be arranged in a cross-type configuration to better control the propulsive force.

Figure 5D:
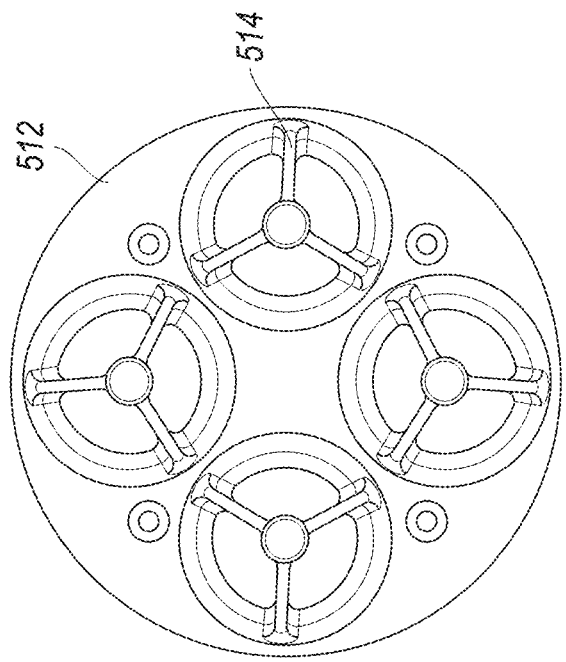
FIG. 5D is an isolated rearward view of the distal element of FIG. 5C.
Figure 5C:
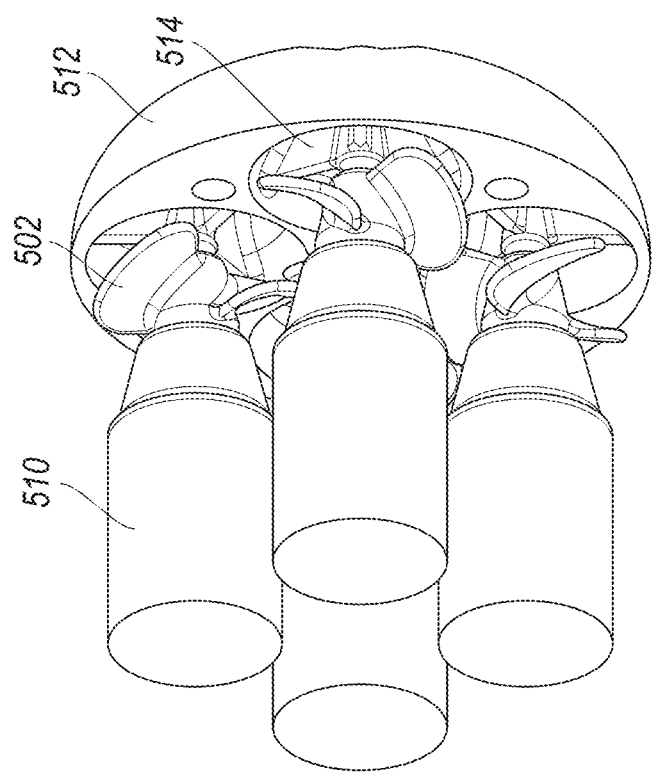
FIG. 5C illustrates how propulsors may be arranged adjacent to stator blades in a distal element of an ingestible device.

FIG. 5D is an isolated, rearward view of the distal element 512 shown in FIG. 5C. In embodiments where the distal element 512 includes multiple stator vanes 514, the stator vanes 514 may be radially arranged around a geometric center of the distal element 512. Generally, the stator vanes 514 are arranged roughly evenly about the geometric center as shown in FIG. 5D. However, in some embodiments, the stator vanes 514 are arranged about the geometric center in an uneven manner.

Figure 6A:
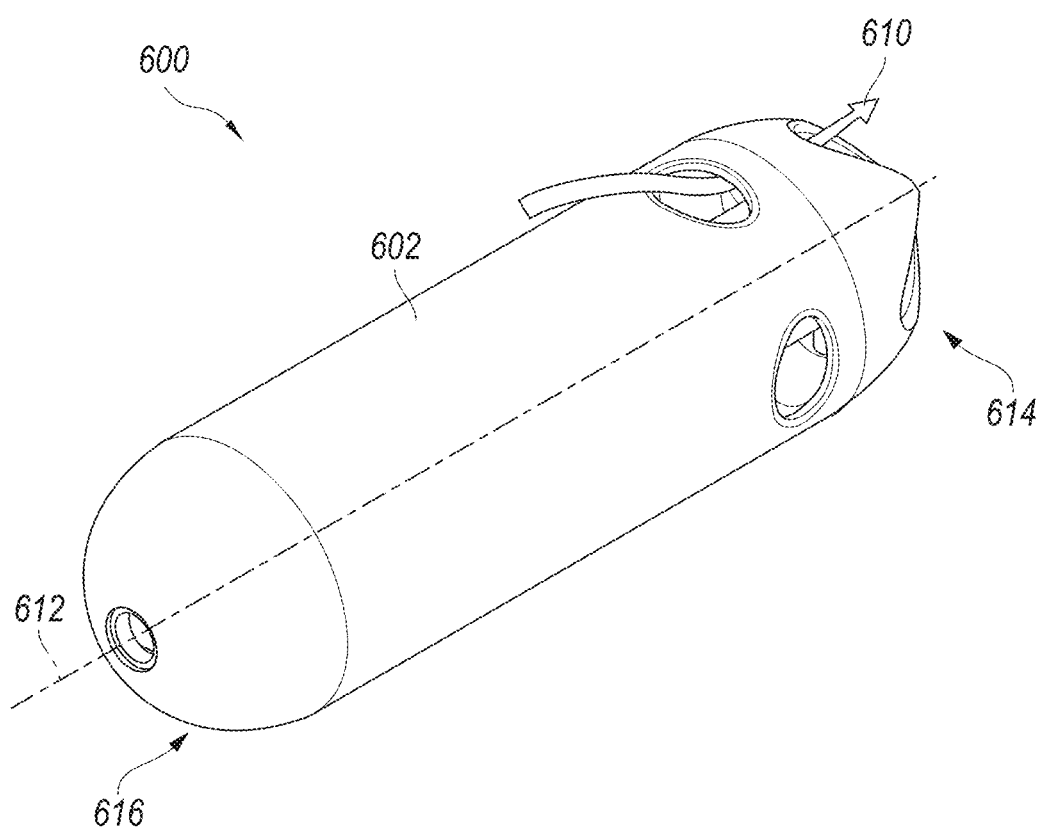
FIG. 6A includes a perspective view of an ingestible device having a rounded structural body with a central axis therethrough.
Figure 6B:
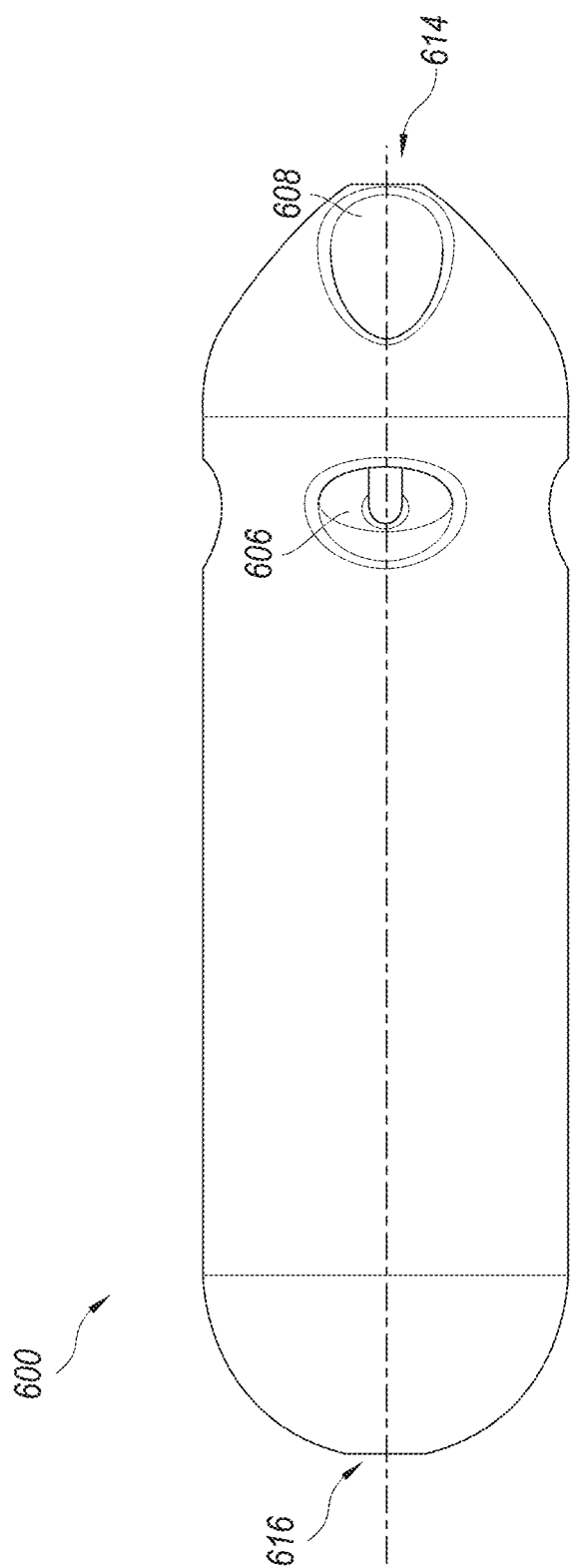
FIG. 6B includes a side view of the ingestible device of FIG. 6A.
Figure 6C:
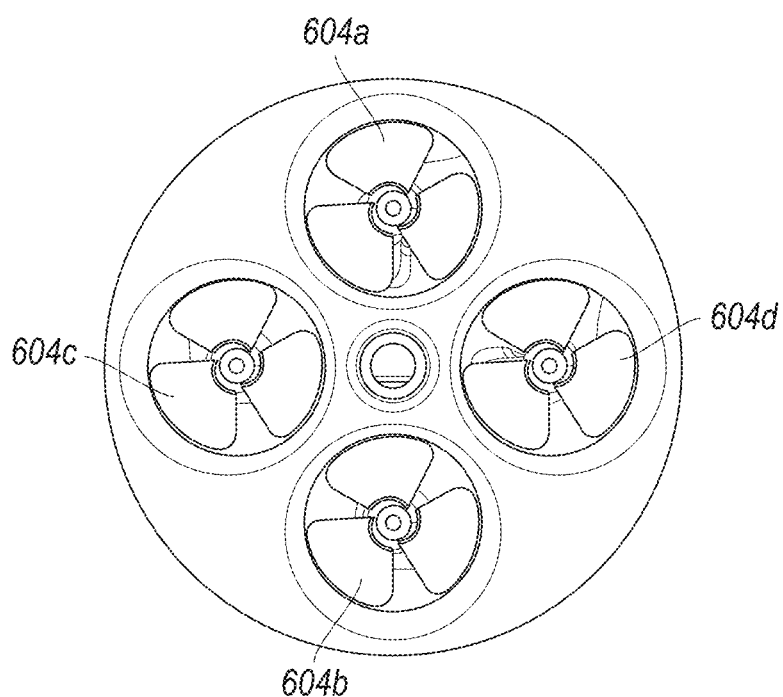
FIG. 6C includes a rear view of the ingestible device of FIG. 6A.

FIGS. 6A-C include perspective, side, and rear views of an ingestible device 600 having an atraumatic structural body 602 with a central axis 612 therethrough. The structural body 602 shown in FIGS. 6A-C is a spherocylinder that includes a cylindrical segment interconnected between hemispherical segments. In other embodiments, the structural body 602 may be in the shape of an oval, rectangle, teardrop, etc.

As noted above, the ingestible device 600 can include one or more propulsors for controlling movement along three mutually perpendicular axes. Here, for example, the ingestible device 600 includes four rotors 604a-d arranged radially about the structural body 602 orthogonal to the central axis 612. The four rotors 604a-d may include a first pair of rotors 604a-b arranged radially opposite each other relative to the central axis 612 and a second pair of rotors 604c-d arranged radially opposite each other relative to the central axis. Each pair of rotors may be configured to share identical chirality; for example, rotors 604a-b may both generate forward thrust when rotating clockwise relative to the central axis 612. Simultaneously, the rotor pairs may be configured to have opposite chirality; for example, rotors 604a-b may generate forward thrust while rotors 604c-d may generate backward thrust when all four rotors are rotating clockwise relative to the central axis 612. As shown in FIG. 6C, the first and second pairs of rotors 604a-d may be arranged in a cross-type configuration so that neighboring rotors rotate in opposite directions to produce thrust in the same direction, while radially opposite rotors rotate in the same direction to produce thrust in the same direction. Such a configuration allows independent control of thrust, pitch, yaw, and roll through the combination of the effects of the individual rotors; thus, control of position and orientation may be achieved in a fashion similar to a quadcopter.

Each rotor may be located in a different channel defined through the structural body 602, and each channel may include an inlet 606 through which fluid is drawn by the corresponding rotor and an outlet 608 through which the fluid is discharged by the corresponding rotor. Generally, the channels are defined through the structural body 602 in a direction substantially parallel to the central axis. Here, for example, the inlet 606 of each channel is located in a cylindrical segment of the structural body 602 while the outlet 608 of each channel is located in a hemispherical segment of the structural body 602. When in operation, the rotors 604a-d can draw fluid through the inlets 606 to create flows 610 that propel the ingestible device in a particular direction. In some embodiments, the channels are tapered. For example, the inlet 606 of each channel may have a smaller diameter than the outlet 608, or the inlet 606 of each channel may have a larger diameter than the outlet 608.

In some embodiments, each rotor is designed to rotate in a primary direction and a secondary direction. For example, the first pair of rotors 604a-b may be configured to be able to rotate in the clockwise and counterclockwise directions in relation to the central axis 612. Similarly, the second pair of rotors 604c-d may be able to rotate in the counterclockwise and clockwise directions in relation to the central axis 612. Accordingly, while the flows 610 are shown as flowing toward a first end 614 (also referred to as the "distal end") of the ingestible device 600, the flows 610 could instead be flowing toward a second end 616 (also referred to as the "proximal end") of the ingestible device 600.

As noted above, the term "rotor," as used herein, refers to a component that is capable of rotating to create propulsive force. The propulsive force imparts momentum to the surrounding fluid(s) to produce movement. The structural body 602 can be fitted with one, two, three, four, or more rotors depending on the speed and maneuvering requirements of the ingestible device 600. In FIGS. 6A-C, for example, four rotors are arranged in a cross-type configuration within the first end 614 of the structural body 602. In other embodiments, three rotors are arranged in a triangular configuration within the first end 614 of the structural body 602.

Each rotor may be independently driven by a different motor. In FIGS. 6A-C, for example, the ingestible device 600 includes four motors configured to supply motive power to the four rotors 604a-d. In other embodiments, multiple rotors may be driven by a single mechanical power converter. For example, a single motor may be responsible for supplying motive power to the first pair of rotors 604a-b, though the speed of these rotors may be varied through a mechanical connection (e.g., a clutch system or a gear system).

In some embodiments, each rotor has a fixed pitch. In FIGS. 6A-C, for example, the four rotors 604a-d are fixedly arranged along a radial plane orthogonal to the central axis 612. In other embodiments, at least one rotor has a variable pitch. In such embodiments, greater control over movement of the ingestible device 600 can be achieved by simultaneously controlling the pitch and rotation of the rotors 604a-d.

The rotors may consist of one or more biocompatible materials. Examples of biocompatible materials include titanium alloys, stainless steel, ceramics, polymers, fiber-reinforced polymers (e.g., fiberglass or carbon fiber) plastics (e.g., polycarbonate, nylon, PEEK, or ABS), resins, composites, etc. Moreover, each rotor may have an antibacterial, hydrophobic, or hydrophilic coating applied thereto. For example, each rotor may be coated with antibiotic-loaded PMMA. The coating(s) applied to the rotors may depend on the type of in vivo environment for which the ingestible device 600 is designed.

Generally, to produce a rotor, a number of blades are secured to the hub through welding, gluing, or, alternatively, by forging the entire rotor in one piece. The number of blades may depend on the desired efficiency, speed, acceleration, maneuverability, etc. For example, 3-blade rotors exhibit good acceleration in comparison to other types of rotors, while 4-blade rotors exhibit good maneuverability in comparison to other types of rotors. Rotors with a higher blade count (e.g., those with 5 or 6 rotor blades) exhibit good holding power in turbulent in vivo environments, such as those with high flow rates. A single-blade rotor may have advantages in manufacturability and durability. In the embodiment shown in FIGS. 6A-C, each rotor includes three helicoidal surfaces acting together to rotate through a fluid (e.g., water, bile, etc.) with a screw effect.

One of the difficulties of producing thrust at small scales is the persistent bubbles that can get trapped near rotors such as propellers, preventing the rotors from properly engaging with the fluid. This problem can be addressed by carefully designing the shape, number, and arrangement of blades along each rotor to assist in the clearing of bubbles. Carefully matching the pitch of the blade, shape of lumens, motor speed, clearance between rotor and wall, clearance between rotor and stator vane, and surface material properties affects the generation and clearing of bubbles.

Rotors may be formed based on simple truncated Archimedes screw geometry. Alternatively, as discussed above, rotors may feature a plurality of individual blades featuring curvature optimized to thrust in the forward or rearward direction. Likewise, if stator blades are positioned in the channels through which the rotors draw and then eject fluid, those stator blades may feature flat or curved blades.

Figure 7B:
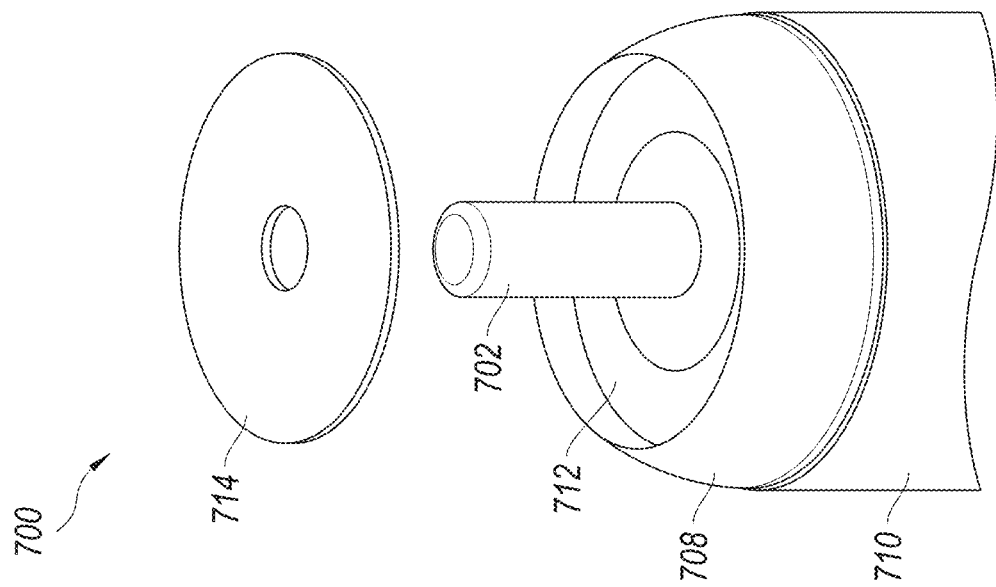
FIG. 7B illustrates how when the seal is potted inside the main seal body, an orifice disc may be secured within the pocket that is formed.
Figure 7A:
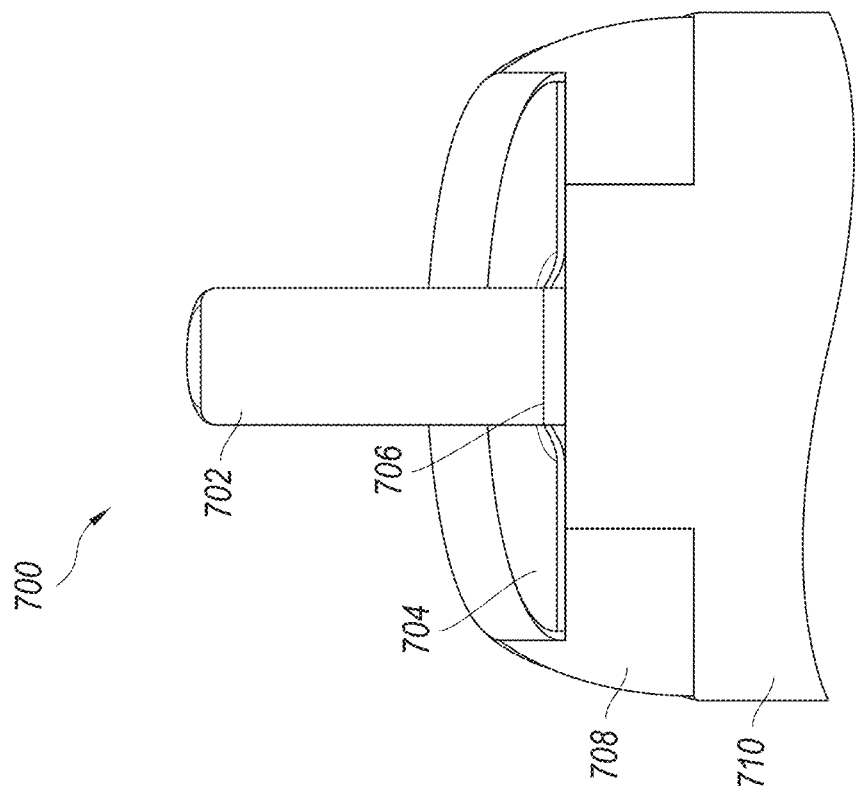
FIG. 7A includes a cross-sectional view of an ingestible device that illustrates how undersizing a seal formed by a punched or drilled sheet compared to the diameter of the motor shaft enables a single contact line to be created between the seal and motor shaft.

Preventing fluid from entering the ingestible device, especially in the propulsion section that includes the moving motor interface, is also critical. Accordingly, the ingestible device may implement tight tolerances, hydrophobic and/or hydrophilic materials, or mechanical seals. Seals can maintain tolerances at the micro scale, and therefore are useful for maintaining safety and consistency without requiring complex assembly processes. FIGS. 7A-B illustrate how low-profile and low-friction seals can be implemented to prevent fluid from entering the motor housing(s) of an ingestible device 700.

FIG. 7A includes a cross-sectional view of the ingestible device 700 that illustrates how undersizing a seal 704 formed by a punched or drilled sheet compared to the diameter of the motor shaft 702 enables a single contact line 706 to be created between the seal 704 and motor shaft 702. Sealing action, static friction, and dynamic friction can be optimized by tuning the dimensional interference and resulting embedded tension. The punched or drilled sheet may be comprised of polytetrafluoroethylene (PTFE) or a similar material (e.g., ultra-high-molecular-weight (UHMW) polyethylene). This design can be readily produced with relatively few machining operations. Another advantage of this approach is that several seals can be produced at once with a simple drilling jig. By under-drilling a small hole (e.g., 0.5-0.6 mm in diameter for a motor shaft that is 0.7 mm in diameter) in the sheet and then dilating it over the motor shaft 702, hoop tension (also referred to as "hoop stress") is produced. The hoop tension will cause the dilated hole to protrude slightly, producing a minimal line of contact 706 with the motor shaft 702 and reducing friction while providing a seal.

The seal 704 can be produced using a hypodermic tubing punch. Multiple seals can be drilled simultaneously on a lathe while still in the hypodermic tube using a simple fixture and drill guide. The assembly process may be completed by placing the seal 704 on the motor shaft 702 and then fixing it in place with a curable adhesive (e.g., a UV-curable adhesive), RF welding, heat welding, etc. The seal 704 can be dilated over the motor shaft 702 and then potted inside a main seal body 708 with a curable adhesive or another sealing technology.

As shown in FIGS. 7A-B, the main seal body 708 may be connected to the motor housing 710 with a curable adhesive or another sealing technology. One or more seals may be implemented on a single motor shaft in order to optimize shaft friction and seal reliability. Successive lip seals with different clearances may assist in optimizing energy efficiency, aging, and overall safety and performance. As shown in FIG. 7B, when the seal 704 is potted inside the main seal body 708, a pocket 712 may be formed. An orifice disc 714 having a hole defined therethrough for receiving the motor shaft 702 may be positioned within the pocket to further inhibit leaking into the motor housing 710. The orifice disc 714 may be comprised of plastic, metal, rubber, Viton, Teflon, UHMW polyethylene, high-density polyethylene, or similar materials.

Accordingly, a manufacturer may obtain a flexible substrate having a substantially circular shape, form a hole at a geometric center of the flexible substrate (e.g., by punching or drilling the hole), and then dilate the hole in the flexible substrate around a motor shaft having a larger diameter than the hole. Such an approach may cause an elastic interference fit to be created between the flexible substrate and motor shaft, thereby forming a seal. Then, the manufacturer may secure the flexible substrate along an outer perimeter to form a hermetic seal. For example, as noted above, the flexible substrate could be secured with a curable adhesive, RF welding, heat welding, etc.

Figure 8A:
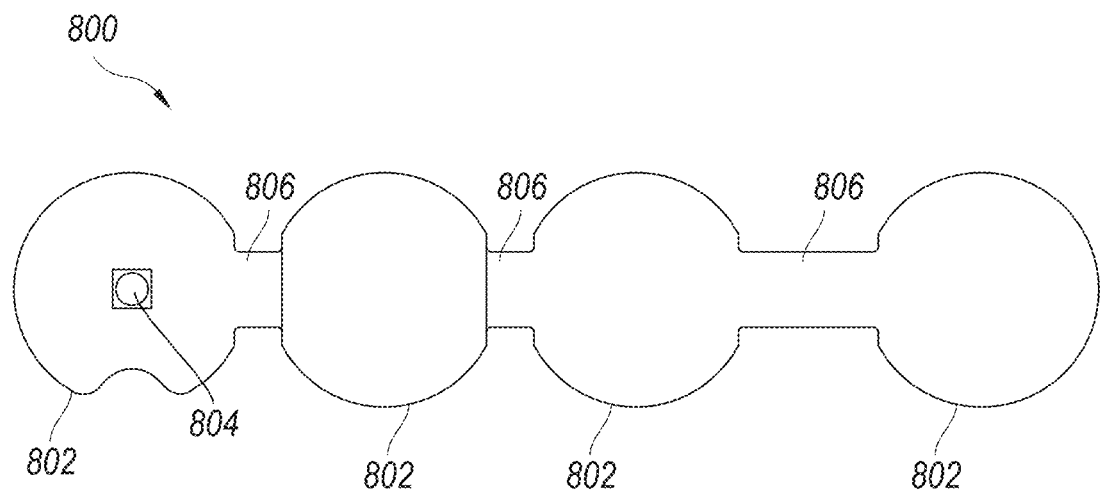
FIG. 8A depicts an example of a flexible printed circuit board assembly (PCBA) in an expanded form.
Figure 8B:
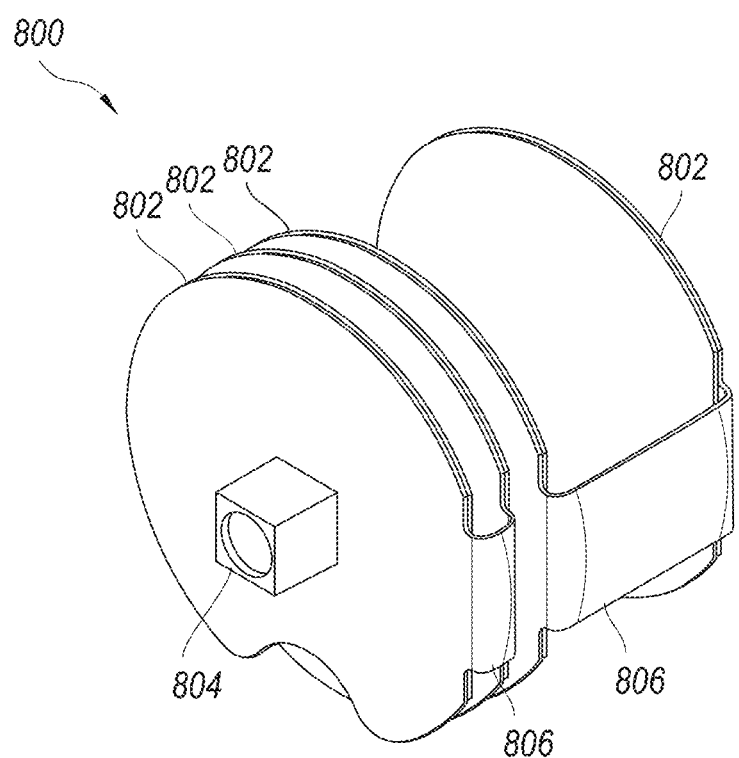
FIG. 8B depicts the flexible PCBA of FIG. 8A in a folded form.

Some or all of the electronic components described herein as being contained within an ingestible device may be mounted on flexible printed circuit board assemblies (PCBAs). FIGS. 8A-B depict an example of a flexible PCBA 800 in its expanded and folded forms, respectively. As shown in FIG. 8A, the flexible PCBA can include at least two rigid areas 802 that serve to provide support to components 804 mounted thereon and accompanying solder joints, as well as to help define the structure of the PCBA 800 as a whole. These rigid areas 802 may be connected by flexible areas 806 that can be folded to allow the PCBA 800 to fit within the ingestible device. The PCBA 800 may include conductive connections between the electronic components to allow for the transfer of power and/or data therebetween. More specifically, the PCBA 800 may include one or more conductive layers that serve as connections between the electronic components mounted to the rigid areas 802. Each pair of conductive layers may be separated by an insulating layer (also referred to as a "non-conductive layer") comprised of a non-conductive material such as polyimide.

Figure 9:
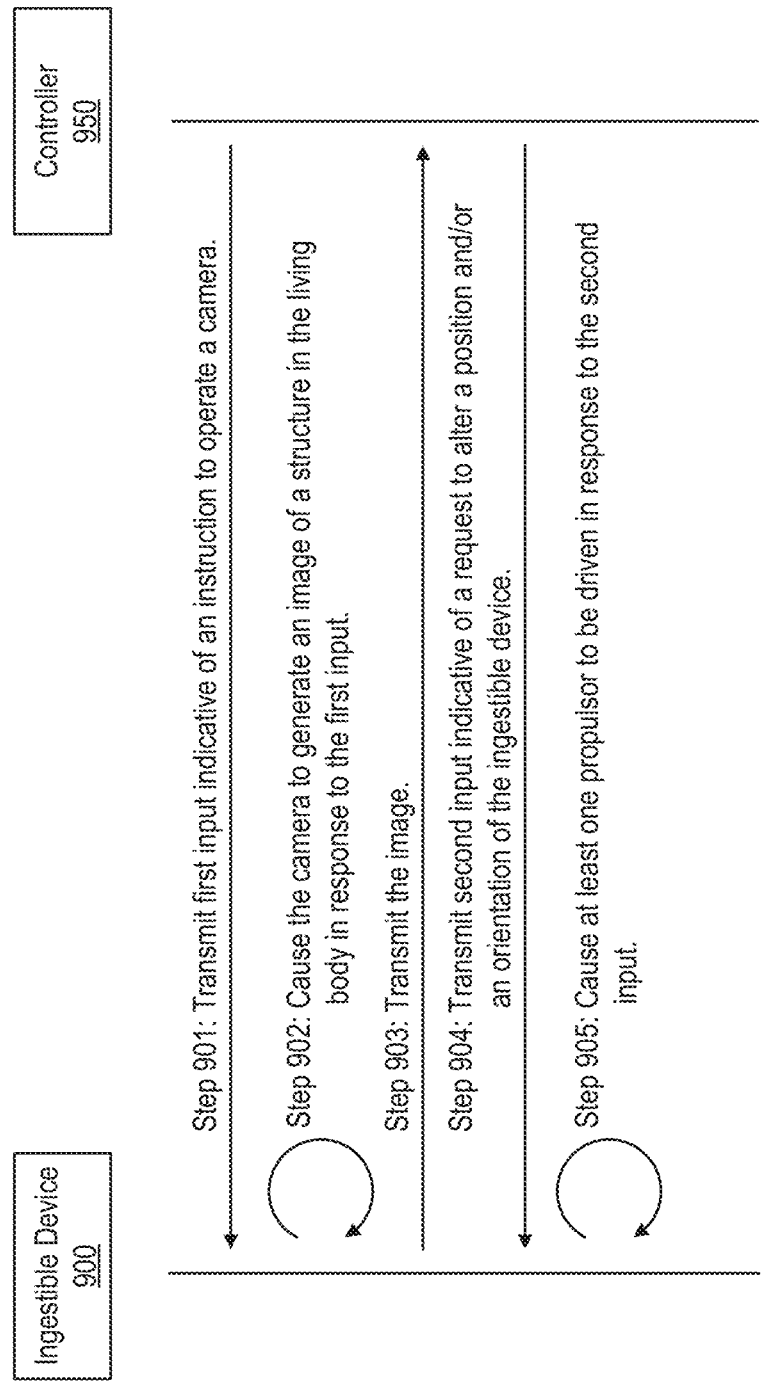
FIG. 9 includes a high-level illustration of communications between a device designed for ingestion by a living body and a controller through which movement of the ingestible device is controlled.

FIG. 9 includes a high-level illustration of communications between a device 900 designed for ingestion by a living body and a controller 950 through which movement of the ingestible device 900 is controlled. Because images generated by the ingestible device 900 may be reviewed on the controller 950, the controller 950 could also be referred to as a "data review station" or "data review unit." Initially, the controller 950 transmits first input indicative of an instruction to operate a camera housed within the ingestible device 900 (step 901). Alternatively, the ingestible device 900 may be designed to automatically operate the camera when the device is first powered on or activated by removal from the packaging.

The ingestible device 900 can cause the camera to generate an image of a structure in the living body in response to the first input (step 902). The structure may be a biological structure or a non-biological structure (also referred to as a "foreign object"). The ingestible device 900 can then transmit the image to the controller 950 for review (step 903). More specifically, a processor responsible for processing images generated by the camera may forward the image to a transmitter for modulation onto an antenna for wireless transmission to the controller. In some embodiments, the transmitter is part of a transceiver capable of transmitting communications to, and receiving communications from, the controller 950.

The controller 950 may further transmit second input indicative of a request to alter a position and/or an orientation of the ingestible device 900 (step 904). This second input may be referred to as a "steering instruction" or a "propulsion instruction." The ingestible device 900 can cause at least one propulsor to be driven in response to the second input (step 905). In instances where multiple propulsors are driven in response to the second input, the ingestible device 900 may generate multiple signals for driving the multiple propulsors. These signals may be different than each other. For example, each propulsor of the multiple propulsors could be rotated at different speeds. As another example, some propulsors of the ingestible device 900 may be rotated while other propulsors of the ingestible device 900 are held stationary.

FIG. 10 depicts a flow diagram of a process 1000 for monitoring an in vivo environment using a device designed for ingestion by a living body. Initially, a subject ingests the ingestible device as part of a capsule endoscopy procedure for observing the gastrointestinal tract (step 1001). The ingestible device (and its controlling software) may support several different data collection modes. For instance, the ingestible device may support a "general mode" suitable for open navigation and/or a "swallow mode" suitable for one-way trips through the esophagus.

An optical sensor included in the ingestible device can then begin generating image data as the ingestible device travels through the living body (step 1002). In some embodiments, the ingestible device causes the optical sensor to begin generating image data in response to receiving an instruction to do so. The instruction may be submitted, for example, by an operator through a controller that is communicatively coupled to the ingestible device. In other embodiments, the ingestible device causes the optical sensor to automatically generate image data in response to determining that a predetermined criterion has been met. For example, the ingestible device may cause the optical sensor to begin generating image data in response to determining that the ingestible device has entered a particular in vivo environment. The ingestible device may reach such a determination by examining biometric data generated by a biometric sensor. For instance, the ingestible device could establish whether it is presently within the stomach by examining biometric data representative of pH measurements. The images may be captured with any of various resolutions, such as 48×48 pixels, 320×240 pixels, or 640×480 pixels. In other embodiments, images may be captured with higher or lower resolutions. The image data may be stored, at least temporarily, in memory located in the ingestible device (step 1003).

The ingestible device can then cause wireless transmission of at least some of the image data to a receiver located outside of the living body via an antenna (step 1004). In some embodiments, the receiver is housed within an electronic device associated with the subject. For example, the image data may be transmitted to a mobile phone associated with the subject, and the mobile phone may forward the image data to another electronic device for review by the operator responsible for controlling the ingestible device. In some embodiments, image data is transmitted to the receiver on a periodic basis (e.g., every 3 seconds, 5 seconds, 30 seconds, 60 seconds, etc.). In other embodiments, image data is transmitted to the receiver in real time. That is, the ingestible device may stream image data to the receiver as the image data is being generated by the optical sensor.

To reduce the amount of raw data that must be transferred across the bus or wireless link, the image data (and well as identifying data, telemetry data, etc.) may be compressed in such a way as to reduce the quantity without significantly affecting user perception of quality. For example, algorithms may be employed that reduce color/hue differently than intensity, or reduce high-frequency content differently than low-frequency content. Standardized image and/or video compression algorithms such as JPEG, H.264 (MPEG), H.265, and the like may be employed to compress the data. To further reduce the amount of data, the image resolution may be reduced before it is compressed and transmitted. For example, the optical sensor may generate an image with 640×480 pixel resolution, but the image may be downsampled to 320×240 pixel resolution prior to JPEG compression. The resolution may be adjusted during operation to achieve a desired tradeoff between image quality and frame rate (e.g., image quality may be reduced in order to increase frame rate while the ingestible device travels through the esophagus). Other compression algorithms may be used after the data has been transmitted over the wireless link, such as in the case where the data is transmitted to a controller that has computing and memory resources available for executing more demanding compression algorithms than is feasible to perform on the ingestible device itself. This additional compression may be used to reduce the size of data that is stored on the controller or some other electronic device. Data may be encrypted, on the ingestible device, the controller, or some other electronic device, to prevent unauthorized third-party access of patient identifying information (PII) or medically sensitive information.

FIG. 11 depicts a flow diagram of a process 1100 for controlling an ingestible device that has an optical sensor as it travels through a living body. Initially, the ingestible device is inserted into the living body (step 1101). For example, if the ingestible device is designed to monitor the digestive system, then the ingestible device may be ingested by a subject. As the ingestible device travels through the living body, the ingestible device may receive first input indicative of an instruction to begin recording image data from a controller located outside the living body (step 1102).

The ingestible device may cause the optical sensor to begin generating image data in response to the first input (step 1103). Alternatively, the optical sensor could be configured to automatically begin generating image data after the ingestible device has been removed from its packaging, or after a mechanical switch accessible along the exterior surface of the ingestible device has been activated. In some embodiments, the ingestible device can be remotely activated by a source located outside the living body via RF signals, magnetic signals, optical signals, etc. For example, the optical sensor may begin generating image data responsive to determining that the ingestible device has been outside of the packaging for a certain amount of time (e.g., 3 minutes, 5 minutes, 10 minutes, etc.). As another example, the optical sensor may begin generating image data responsive to determining that the ingestible device has entered a particular in vivo environment.

The ingestible device can then wirelessly transmit at least some of the image data to a receiver using an antenna (step 1104). For example, a processor may transmit the image data to a transceiver responsible for modulating the image data onto the antenna for transmission to the receiver. In some embodiments, the image data is transmitted in its original (i.e., raw) form. In other embodiments, the image data is transmitted in a processed form. For example, the processor may filter values from the image data, add metadata (e.g., specifying a location, time, or identifier associated with the living body), etc. As noted above, the receiver may be part of the controller or some other electronic device. For example, a medical professional may view the image data and control the ingestible device using a mobile workstation that is wirelessly connected to the ingestible device. As another example, a medical professional may view the image data on a tablet computer and control the ingestible device using a dedicated input device that is similar to controllers for video game consoles.

In some instances, the medical professional may wish to view a particular structure in the living body. Accordingly, the ingestible device may receive a second input indicative of an instruction to move so that the structure can be observed by the optical sensor (step 1105). Said another way, the ingestible device may move so that the structure is located in a field of view (FoV) of the optical sensor. The ingestible device may move by altering its position and/or orientation. The ingestible device may determine the appropriate driving signal for each propulsion component based on the desired position and/or characteristics of the in vivo environment, such as viscosity, flow rate, pressure, temperature, etc. Once the ingestible device has reached the desired position, the ingestible device may automatically maintain its position until a predetermined interval of time expires or until an instruction to move to a new position is received from the controller.

The ingestible device can then cause at least one propulsor to be driven in response to the second input (step 1106). In some embodiments, the propulsor(s) are driven based entirely on the second input. For example, if the second input is representative of an instruction to move forward, the propulsor(s) can be driven to achieve forward movement.

For embodiments of the ingestible device that are powered using an onboard battery, it is generally desirable to minimize battery discharge before the ingestible device is ready to be used in order to maximize the amount of power available during operation. To avoid battery drain during shipping and storage prior to deployment, the ingestible device may enter a low-power inactive state where current drawn from the battery is minimized or the battery is disconnected from other components (e.g., with a mechanical switch, a transistor such as a MOSFET, or some other means). To leave this state, the ingestible device may be activated by a sensor.

Some embodiments of the ingestible device employ a photosensor that prompts activation when light is detected. The photosensor may be configured to generate readings indicative of the level of visible, infrared, or ultraviolet light that is presently detectable. In these embodiments, the ingestible device may be shipped and stored in a substantially opaque package to prevent the photosensor from being activated inadvertently or prematurely. When the package is opened, the photosensor will be exposed to light and the ingestible device can be activated. Other embodiments of the ingestible device employ a low-power magnetic sensor that activates when the ingestible device is exposed to a magnetic field. Alternatively, the ingestible device may include a low-power magnetic sensor that activates when the ingestible device is not exposed to a magnetic field. For instance, a magnet may be included in the packaging so that the ingestible device is exposed to a magnetic field at all times while being shipped and stored. This embodiment has several advantages. First, there is minimal risk of premature activation since the packaging is likely to accompany the ingestible device until deployment is imminent. Second, the individual responsible for deploying the ingestible device does not need to introduce an activation signal such as a magnetic field. Other embodiments of the ingestible device may use a reed relay as a mechanical power switch to activate the ingestible device upon being exposed to a magnetic field. In embodiments where the ingestible device is activated by exposure to a magnetic field, a single- or multiple-use magnetic fixture could be used to facilitate activation by holding the magnet in the correct orientation with respect to the ingestible device. Other embodiments of the ingestible device may be activated by a mechanical element (e.g., a switch or button) that is sealed to prevent fluid ingress but is located along the exterior surface of the enclosure so as to be accessible.

As discussed above, the ingestible device may have built-in features, such as sensors, software, and the like, for performing self-diagnostic tests. Using these built-in features, health and performance functions of the ingestible device can be regularly tested. These built-in features can also help in debugging and exploring new operational regimes. Examples of self-diagnostic tests include checksum errors, software versioning, battery voltage, power draw per motor, tests of other major components, etc. Alternately or additionally, the camera may be commanded to generate a test image (e.g., of packaging) to be transmitted to a destination (e.g., the controller), where it may be compared to an expected reference image. Successful transmission of the test image would require the ingestible device be functioning properly. If the test image is not received or is not correct, it could signify a defect (e.g., in the ingestible device, communication channel, etc.) for which an alert may be generated that indicates that the ingestible device should not be deployed.

Manipulation of Structures in a Living Body

The ability to manipulate the surrounding environment while an ingestible device is located in a living body can be useful. For example, while traveling through a living body, an ingestible device may generate images of a structure that merits further examination. The structure may be tissue, or the structure may be a foreign body of unknown origin. In this situation, the operator of the ingestible device may wish to perform advanced diagnostics beyond simply analyzing the images of the structure. Such diagnostics can be performed if the ingestible device includes one or more intervention tools (also referred to as "intervention components" or "intervention mechanisms") as further discussed below.

For the purpose of simplification, ingestible devices may be described as having a single intervention component. However, ingestible devices such as those described herein may include multiple intervention components that are able to manipulate structures in living bodies in different ways. For example, an ingestible device may include a biopsy appendage able to gather samples and a cauterization mechanism able to close wounds resulting biopsies. Accordingly, unless otherwise specified, embodiments of ingestible devices could include any combination of the intervention components described herein.

Figure 12:
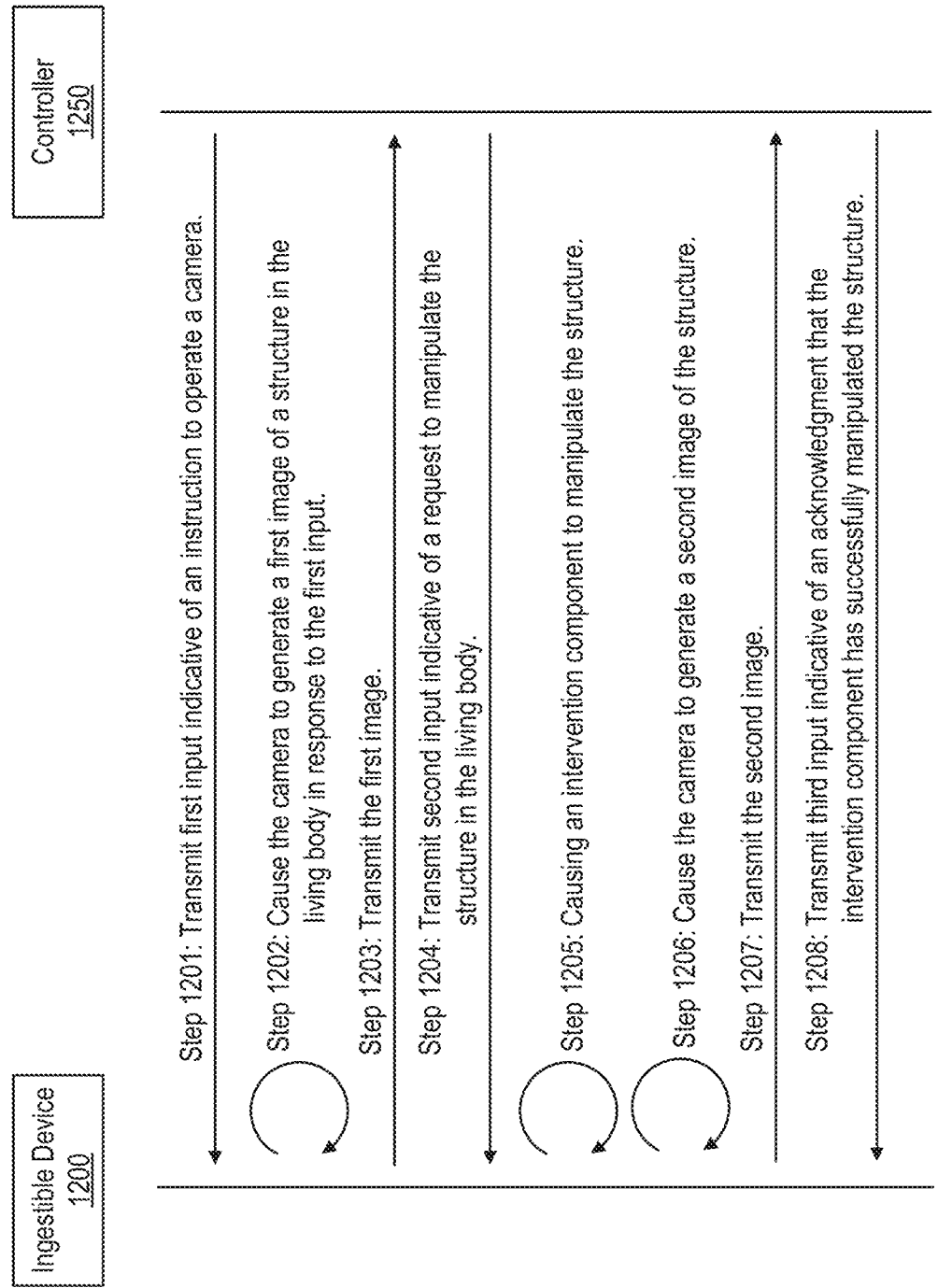
FIG. 12 includes a high-level illustration of communications between an ingestible device that has an intervention component for manipulating the surrounding environment and a controller through which the intervention component can be controlled.

FIG. 12 includes a high-level illustration of communications between an ingestible device 1200 that has an intervention component for manipulating the surrounding environment and a controller 1250 through which the intervention component can be controlled. Steps 1201-1203 may be the same as or substantially similar to steps 901-903 of FIG. 9. In this scenario, however, the controller 1250 transmits second input indicative of a request to manipulate the structure to the ingestible device 1200 (step 1204).

Upon receiving the second input, the ingestible device 1200 can cause an intervention component to manipulate the structure (step 1205). In some embodiments, the intervention component is arranged along the exterior surface of the ingestible device 1200 (e.g., within a depression in the capsule), and thus can simply be extended toward the structure. In other embodiments, the intervention component is arranged in a cavity inside the ingestible device 1200. In such embodiments, the intervention component can be extended toward the structure through an aperture in the capsule. An operator may be able to control the intervention component through the controller 1250. Thus, the ingestible device 1200 may control the intervention component based on input provided by the operator through the controller 1250. For example, the operator may be permitted to control the intervention component through a control mechanism, such as a joystick, that is connected to the controller 1250.

In some embodiments, the ingestible device 1200 causes the camera to generate a second image of the structure while the intervention component is manipulating the structure (step 1206) and then transmits the second image to the controller 1250 for review by the operator (step 1207). The operator may be a medical professional, such as a general practitioner, nurse, or specialist (e.g., a surgeon or gastroenterologist), that is responsible for managing the ingestible device 1200. By comparing the first and second images, the operator can determine whether the structure has been successfully manipulated. In some embodiments, the second image is part of a series of images that are streamed to the controller 1250 in real time while the intervention component is in use. For example, the ingestible device 1200 may stream a series of images to the controller 1250 throughout a procedure so that the operator can determine how to control the intervention component, whether the procedure was successful, whether the ingestible device 1200 should be repositioned, etc.

Thereafter, the controller 1250 can transmit third input indicative of an acknowledgement that the intervention component has successfully manipulated the structure (step 1208). The acknowledgement may be submitted through the controller or some other electronic device by the operator. In some embodiments, the acknowledgement is explicit. For example, the operator may specify that the structure has been successfully manipulated by interacting with a digital element shown on a display to which the controller 1250 is communicatively coupled. In other embodiments, the acknowledgement is implicit. For example, the operator may request that the intervention component be moved to a new position, which indicates that the structure has been successfully manipulated.

Alternatively, the acknowledgement may be generated by a sensor that monitors whether the intervention component successfully manipulated the structure. For example, the ingestible device 1200 may include a biopsy appendage that can be used to gather samples as further discussed below. In such embodiments, the ingestible device 1200 may include a sensor (e.g., an acoustic sensor or optical sensor) that determines whether the biopsy appendage includes a sample based on reflected energy. As another example, the biopsy appendage may include a pressure sensor that is arranged such that acquisition of the sample will cause pressure to be applied to the pressure sensor.

Figure 13:
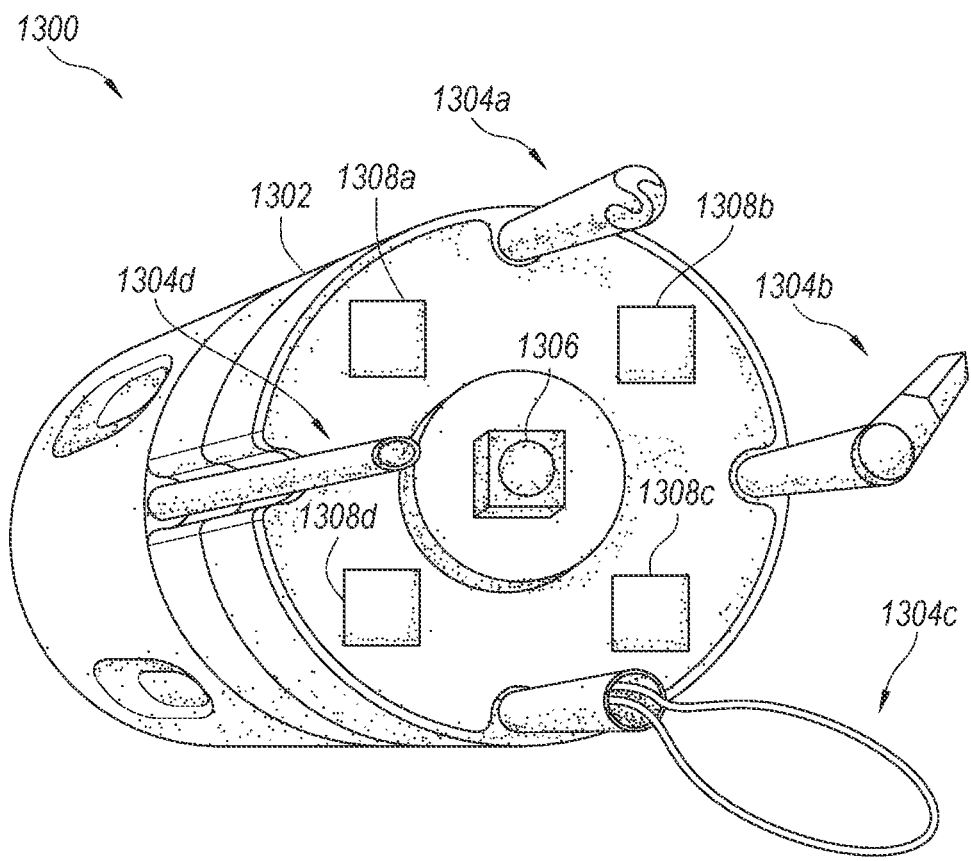
FIG. 13 is a perspective view of an ingestible device with a plurality of intervention components located at the proximal end of a capsule.

FIG. 13 is a perspective view of an ingestible device 1300 with a plurality of intervention components 1304*a-d* located at the proximal end of a capsule 1302. In FIG. 13, the ingestible device 1300 includes four intervention components that are spaced circumferentially about the capsule 1302. However, other embodiments may include greater than four intervention components or fewer than four intervention components. For example, an ingestible device may include a pair of intervention components located on opposing sides of the capsule 1302.

The plurality of intervention components 1304*a-d* may be representative of tools that are complementary to one another. Thus, each intervention component of the plurality of intervention components 1304*a-d* may be able to manipulate the environment surrounding the ingestible device 1300 in a different way. This need not necessarily be true, however. For example, an ingestible device may include a pair of intervention components (e.g., on opposing sides of the capsule 1302) configured for grasping and another intervention component configured to sampling, cutting, cauterizing, etc.

In FIG. 13, the ingestible device 1300 includes a biopsy mechanism 1304*a*, a delivery mechanism 1304*d* able to deliver having material stored therein, and a pair of grasping mechanisms 1304*b-c*. Biopsy mechanisms (also referred to as "biopsy appendages" or "biopsy implements") can be used to obtain samples from a living body to discover the presence, cause, or extent of a disease. Delivery mechanisms (also referred to as "delivery implements") can have materials stored therein, such as medications, cauterization agents, radiation enhancement agents, and inks. The term "medication," as used herein, may refer to any substance that could be used for treatment regardless of its form. Examples of medications include therapeutic medicines, drugs, and natural and bioidentical hormones. Meanwhile, grasping mechanisms (also referred to as "grasping implements") can be used to grasp structures in the living body. In FIG. 13, the pair of grasping mechanisms includes a manipulator arm 1304*b* and a polypectomy implement 1304*c*.

The ingestible device 1300 may include a camera 1306 that is able to captures images of the surrounding environment before, during, or after manipulation by the intervention components 1304*a-d*. As shown in FIG. 13, the plurality of intervention components 1304*a-d* may be spaced radially around the camera 1306 in an even manner. Alternatively, the plurality of intervention components 1304*a-d* may be spaced radially around the camera 1306 in an uneven manner. For example, a pair of intervention components may be located proximate each other along one side of the capsule 1302 while another intervention component may be located along the other side of the capsule 1302. As another example, a first pair of intervention components may be located proximate each other along one side of the capsule 1302 while a second pair of intervention components may be located proximate each other along the other side of the capsule 1302.

As discussed above, the ingestible device 1300 can include illumination source(s) that emit electromagnetic radiation into the surrounding environment. These illumination source(s) may be arranged around the camera 1306 to provide consistent illumination of the surrounding environment. In FIG. 13, a plurality of illumination sources 1308*a-d* are spaced radially about the camera in an even manner, though the plurality of illumination sources 1308*a-d* are offset from the plurality of intervention components 1304*a-d*.

Figure 14:
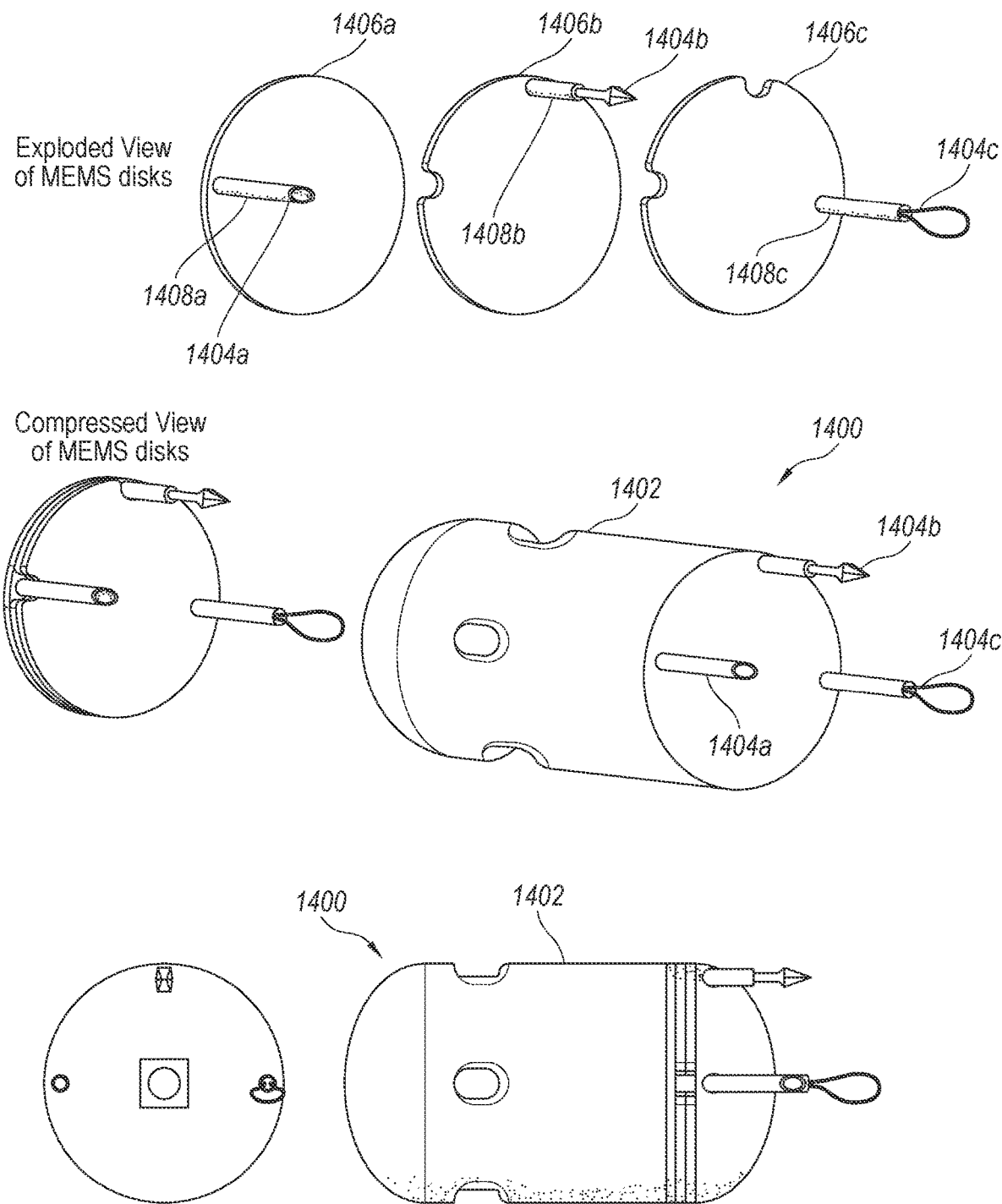
FIG. 14 illustrates how each intervention component in an ingestible device may be mounted on a separate disk contained inside the capsule.
Figure 15:
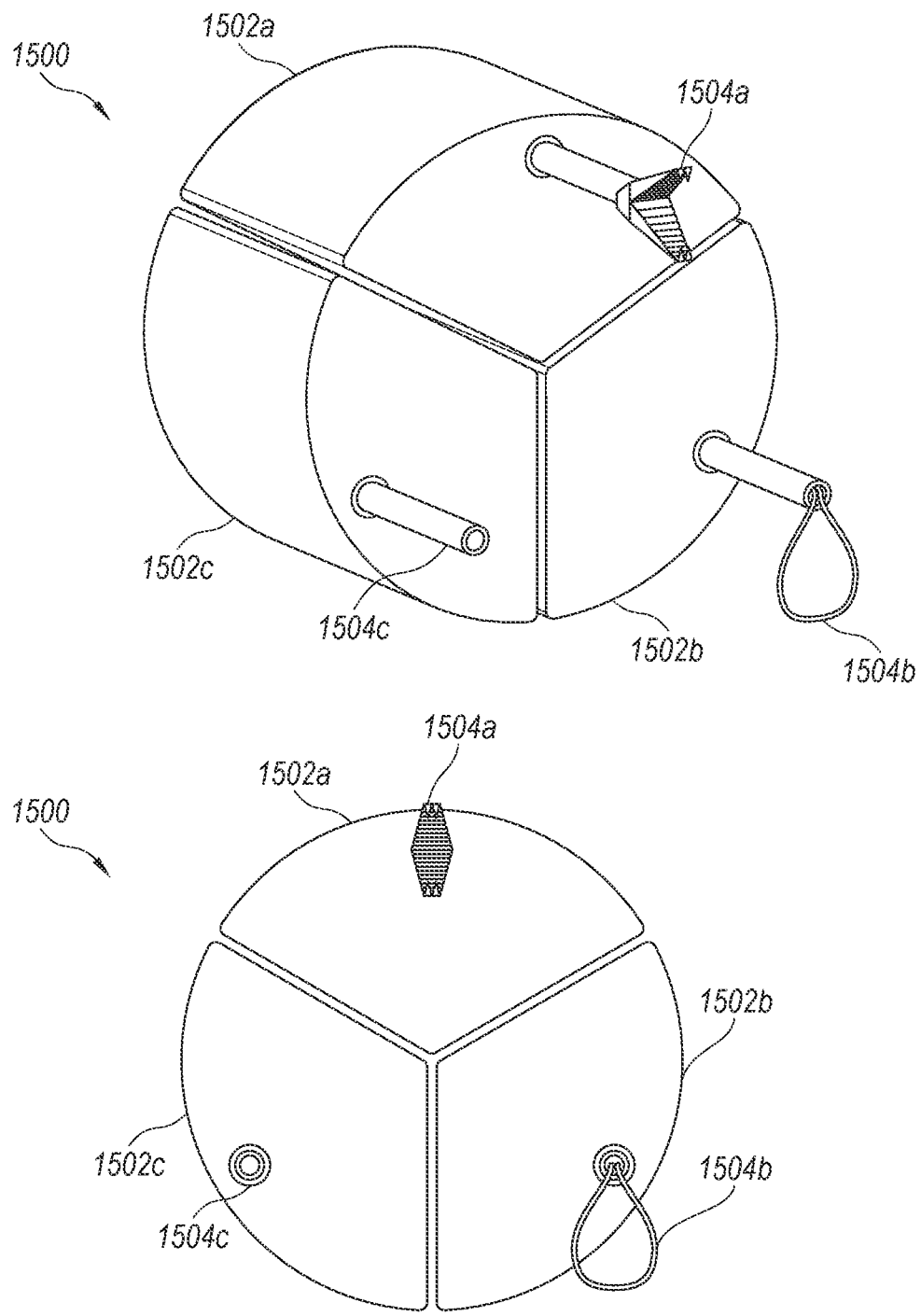
FIG. 15 includes perspective and end views of a radial arrangement of bays that contain the driving mechanism(s) needed for corresponding intervention components.

Intervention components can be installed within an ingestible device in several different ways. FIGS. 14-15 illustrate two different approaches to installing intervention components inside a capsule.

FIG. 14 illustrates how each intervention component in an ingestible device 1400 may be mounted on a separate disk contained inside the capsule 1402. Each disk can include the mechanism(s) needed to drive or actuate the corresponding intervention component. For example, each disk may include a dedicated controller that is communicatively coupled to the processor of the ingestible device 1400 from which instructions to operate are received. Additionally or alternatively, each disk may include driver(s), electric motor(s), and the like. In other embodiments, these disks include microelectromechanical systems (MEMS) devices for operating the corresponding intervention component, and therefore may be referred to as "MEMS disks."

As discussed above, an intervention component may reside entirely within the capsule 1402 while in a retracted state. While in the extended state, however, the intervention component may at least partially reside outside of the capsule 1402. FIG. 14 includes end, side, and perspective views of the ingestible device 1400 with all of the intervention components 1404*a-c* in the extended state.

Generally, the disks 1406*a-c* are secured in a longitudinally stacked arrangement inside the capsule 1402. Each disk may have a longitudinally oriented tube 1408*a-c* that extends toward either the proximal or distal end of the ingestible device 1400 through which the intervention component can be delivered. To accommodate these tubes 1408*a-c*, at least some of the disks 1406*a-c* may include clearance feature(s) through which the tubes of underlying disks can be routed. In FIG. 14, for example, the lowermost MEMS disk 1406*a* has zero clearance features, the uppermost MEMS disk 1406*c* has two clearance features, and the middle MEMS disk 1406*b* has one clearance feature. One example of a clearance feature is a notch along a periphery of the disk, while another example of a clearance feature is an aperture in the disk. Clearance features enable the disks 1406a-c to be stacked in a volumetrically efficient and modular arrangement. Such an approach allows new intervention components to be readily developed and integrated without completely redesigning the architecture of the ingestible device 1400.

FIG. 15 includes perspective and end views of a radial arrangement 1500 of bays 1502a-c that contain the driving mechanism(s) needed for corresponding intervention components 1504a-c. As shown in FIG. 15, each intervention component may be linearly advanced between a retracted state and an extended state. The radial arrangement 1500 of bays 1502a-c may occupy a full 360-degree sweep inside the capsule. Alternatively, there may be an interruption between these bays for other components. For example, the bays 1502a-c may be designed such that, when joined together, a channel for cables (e.g., for the camera and illumination sources) is formed at a geometric center of the radial arrangement 1500. As another example, the bays 1502a-c may be designed such that, when joined together, a channel for cables is formed between each pair of bays.

In some embodiments, the available radial space is divided into roughly equal areas to ensure modularity in design. In such embodiments, intervention components may be designed with standard radial widths to ensure occupation of these bays is possible. Similar to the approach shown in FIG. 14, the approach shown in FIG. 15 allows new intervention components to be readily developed and integrated without completely resigning the architecture of the ingestible device.

Figure 16:
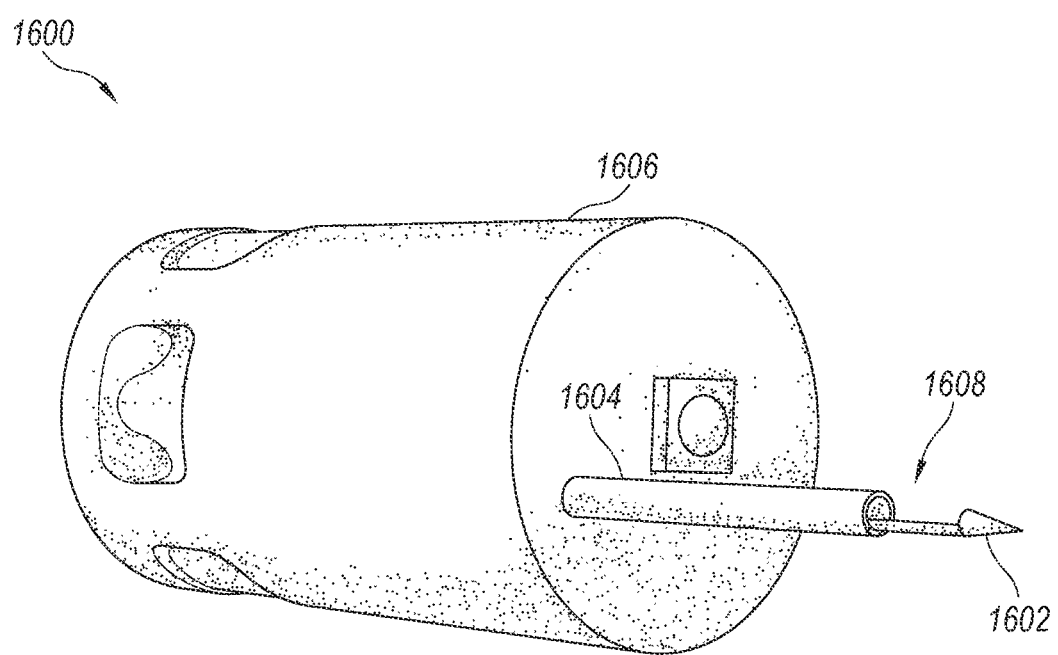
FIG. 16 includes a perspective view of an ingestible device with a biopsy mechanism capable of removing a sample from a structure in a living body and then storing the sample for further analysis.

FIG. 16 includes a perspective view of an ingestible device 1600 with a biopsy mechanism 1602 capable of removing a sample from a structure in a living body and then storing the sample for further analysis. For example, the biopsy mechanism 1602 may retain the sample so that the sample can be removed for further analysis after the ingestible device 1600 is no longer inside the living body. The sample may be taken from an anatomical structure, or the sample may be taken from a foreign body. After approaching the structure, the ingestible device 1600 may cause the biopsy mechanism 1602 to extend from the capsule 1606 toward the structure. For example, the ingestible device 1600 may cause the biopsy mechanism 1602 to be extended through an aperture 1604 in the capsule 1606 as shown in FIG. 16.

In some embodiments, the biopsy mechanism 1602 comprises a hollow structural body with a tapered tip at the distal end as shown. The hollow structural body can comprise stainless steel, titanium alloy, or another rigid, biocompatible material. When the tapered tip of the hollow structural body is inserted into the structure, a portion of the structure may enter the hollow structural body through a lateral opening 1608. This type of biopsy mechanism may be referred to as a "plunging-type element." Then, the ingestible device 1600 may receive input indicative of an acknowledgement that the biopsy appendage 1602 successfully gathered the sample. In some embodiments the acknowledgement is generated by a sensor configured to monitor whether the biopsy appendage includes the sample, while in other embodiments the acknowledgement is submitted by an operator via a controller with which the ingestible device 1600 is controlled. For example, the operator may provide the acknowledgement upon determining, based on analysis of images generated by the ingestible device 1600, that the biopsy mechanism 1602 entered the structure to a sufficient depth. Upon receiving the input, the ingestible device 1600 can cause the biopsy mechanism 1602 to be retract from the structure through the aperture 1604 in the capsule 1606 with the sample lodged in the lateral opening 1608.

In other embodiments, the biopsy mechanism 1602 includes a needle that comprises a hollow structural body with a sharpened tip at the distal end. In such embodiments, the ingestible device 1600 can cause the needle to extend toward the structure such that the sharpened tip enters the structure and then retract such that the sharpened tip withdraws from the structure. The hollow structural body may include one or more barbs along its inner surface to facilitate in securing the sample. For example, an annular arrangement of barbs may be spaced circumferentially about the inner surface of the hollow structural body. While these barb(s) may be passive structural elements, each barb can be oriented in such a manner that movement of samples in one direction is inhibited or restricted. For example, the barb(s) may be oriented in such a manner to allow a sample to readily enter the hollow structural body but inhibit removal of the sample from the hollow structural body (e.g., when the sharpened tip of the needle is withdrawn from the structure from which the sample is taken).

Figure 16A:
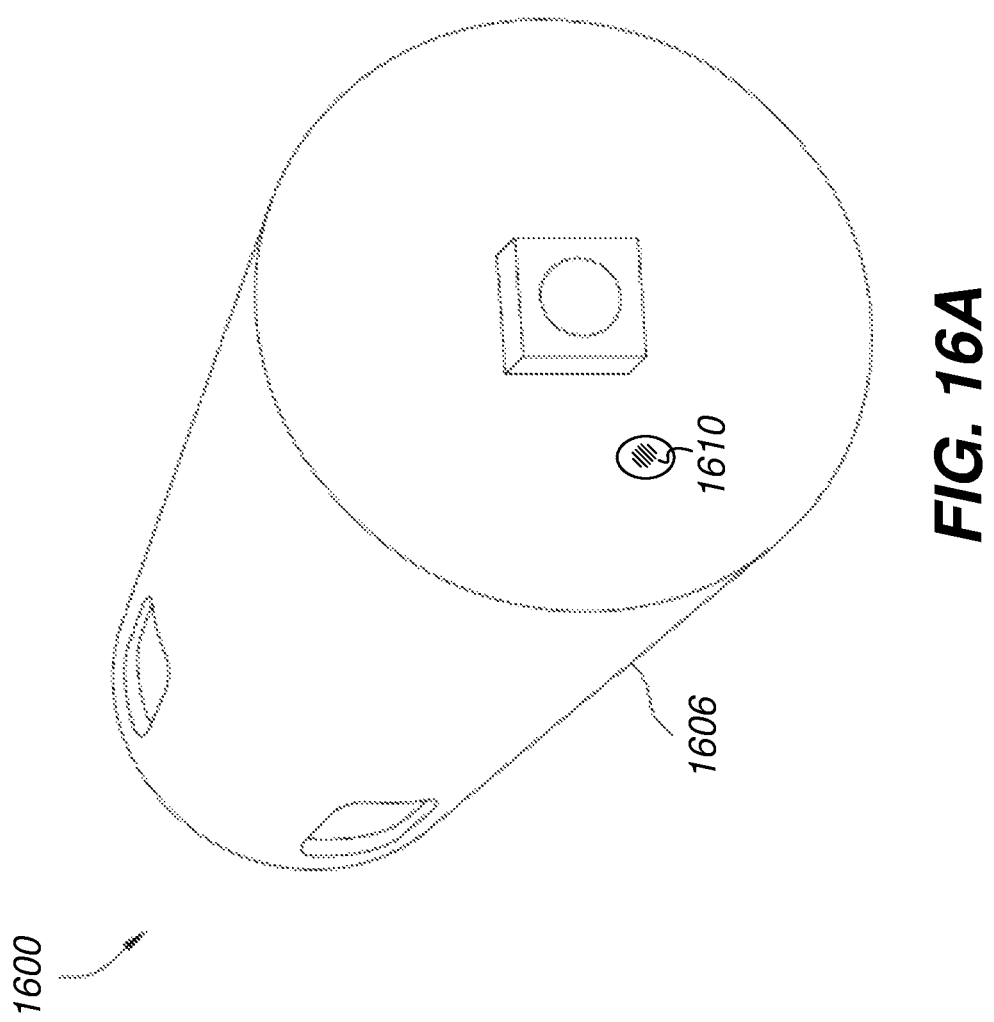
FIG. 16A includes a perspective view of an ingestible device with a barrier that is configured to inhibit exposure of the biopsy mechanism to the surrounding environment.

The ingestible device 1600 may include a barrier, illustrated as barrier 1610 in FIG. 16A, that is configured to inhibit exposure of the biopsy mechanism 1602 to the surrounding environment by restricting access through the aperture 1604 in the capsule 1606. Said another way, the barrier may inhibit entry of fluid into the capsule 1606 by occluding the aperture 1604.

In some embodiments, the barrier comprises a rigid material such as a polymer or metal. In its original position, the barrier may completely occlude the aperture 1604 to prevent ingress of fluids (and egress of the biopsy mechanism 1602). A deployment mechanism can be configured to move the barrier before the biopsy appendage 1602 is extended through the aperture 1604. The deployment mechanism could achieve movement via solenoid action, rack and pinion action (e.g., an electric motor with corresponding gears), spring loading, pneumatic loading, hydraulic loading, etc. Generally, the deployment mechanism moves the barrier so that the aperture 1604 is completely open accessible; however, the deployment mechanism could move the barrier so that a portion of the aperture 1604 remains occluded.

In other embodiments, the barrier comprises an elastomer such as an unsaturated rubber (e.g., isoprene rubber) or a saturated rubber (e.g., silicone rubber). In such embodiments, a deployment mechanism may move the biopsy mechanism 1602 to the extended position without moving the barrier, thereby causing the barrier to be punctured by the biopsy mechanism 1602. Alternatively, the barrier may include an opening (e.g., a slit) through which the deployment mechanism can move the biopsy mechanism 1602 without damaging the barrier. Elastomer-based barriers may be desirable in some circumstances as longitudinal movement of the biopsy mechanism 1602 is possible while still maintaining some sealing action against fluids.

As further discussed below, other intervention components may be present to facilitate collection of the sample. For example, embodiments of the ingestible device 1600 may include drill bits with high rake angles (e.g., for peeling of samples), grasping mechanisms, or cutting mechanisms with sharpened edges to help remove the sample from the structure. As another example, the ingestible device may include a brush with bristles (e.g., having micro barbs) that can be scraped across the surface of the structure to obtain the sample. For instance, the brush may be subjected to rotational or linear motion to scrape cells from tissue of interest.

Figure 17:
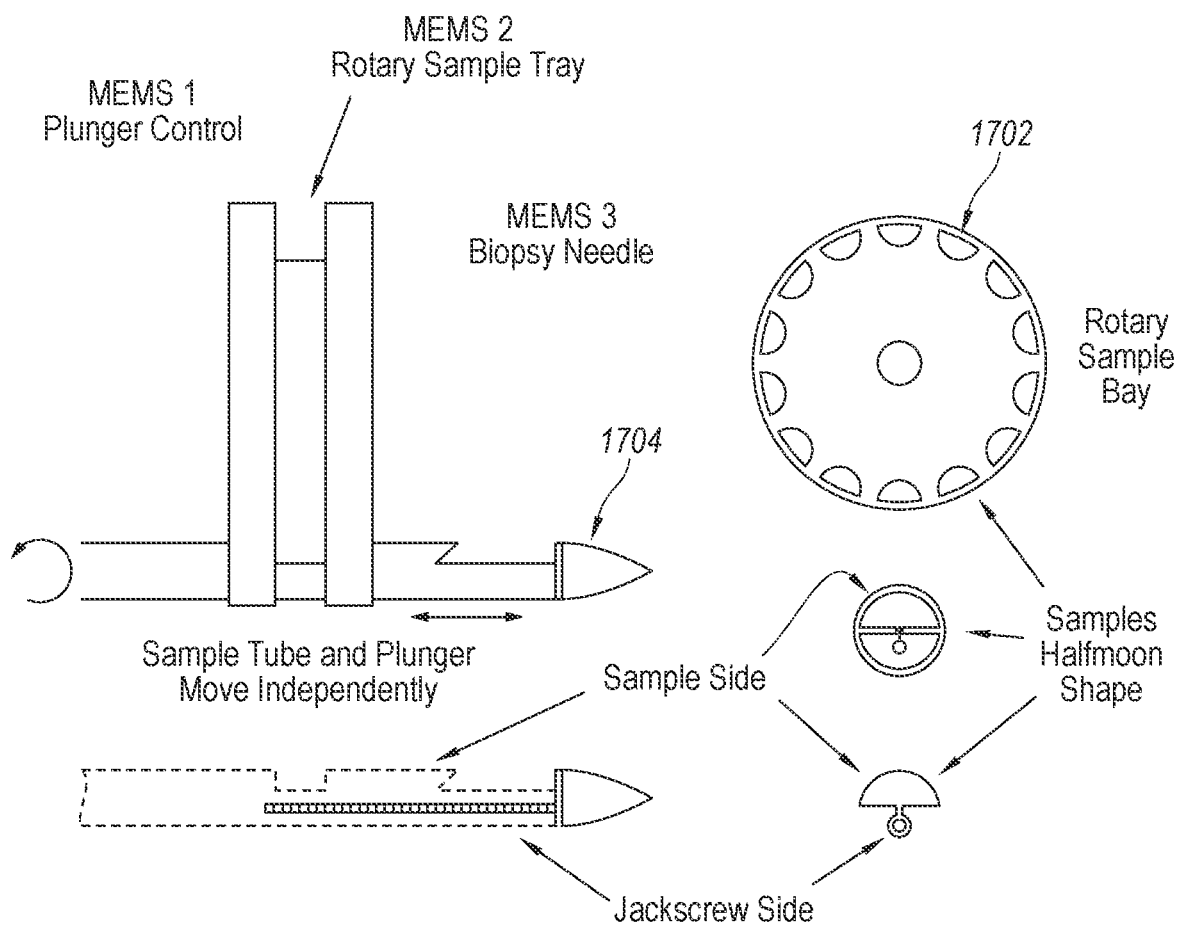
FIG. 17 illustrates how an ingestible device may include one or more storage bays in which samples can be sealed.

FIG. 17 illustrates how an ingestible device may include one or more storage bays 1702 in which samples can be sealed. As discussed above, an ingestible device can include an intervention component 1704 capable of obtaining samples from structures in a living body. For example, an ingestible device may include a needle with a sharpened tip that can be inserted into a structure from which a sample is to be taken, or an ingestible device may include a plunging-type element (e.g., on a jackscrew) that can be plunged into the structure from which a sample is to be taken. In FIG. 17, the intervention component 1704 is a plunging-type element similar to the biopsy mechanism of FIG. 16; however, those skilled in the art will recognize that various types of intervention components could be employed by the ingestible device to gather samples. Regardless of its form, the intervention component can be retracted into the capsule with a sample.

A collection mechanism may be configured to remove the sample from the intervention component 1704 for storage in one of the storage bays. For example, a vacuum element may pull the sample into one of the storage bays, or a mechanical element may push or place the sample into one of the storage bays. Such an approach allows multiple samples to be obtained and then isolated, both from one another and the surrounding environment, while the ingestible device travels through a living body.

As shown in FIG. 17, the ingestible device may include a radial arrangement of storage bays 1702 that can be rotated as samples are gathered by an intervention component. For example, after a sample has been removed from the intervention component 1704 and stored in one of the storage bays 1702, the radial arrangement may rotate so that the sample gathered by the intervention component 1704 can be stored in another storage bay. The ingestible device may be designed in such a way that the capsule can be opened (e.g., with a proprietary tool) and the samples in the storage bays 1702 can be removed after the ingestible device has left the living body.

Other embodiments of the ingestible device include a radial arrangement of storage bays, where each storage bay is associated with a corresponding intervention component. In such embodiments, the sample gathered by each intervention component can be stored in its own storage bay to minimize the likelihood of cross contamination. As discussed above, these intervention components may be separately controlled by dedicated driving mechanisms, or these intervention components may be rotated through a single driving mechanism as samples are collected and the ingestible device is cycled to prepare for collection of the next sample.

Figure 18A:
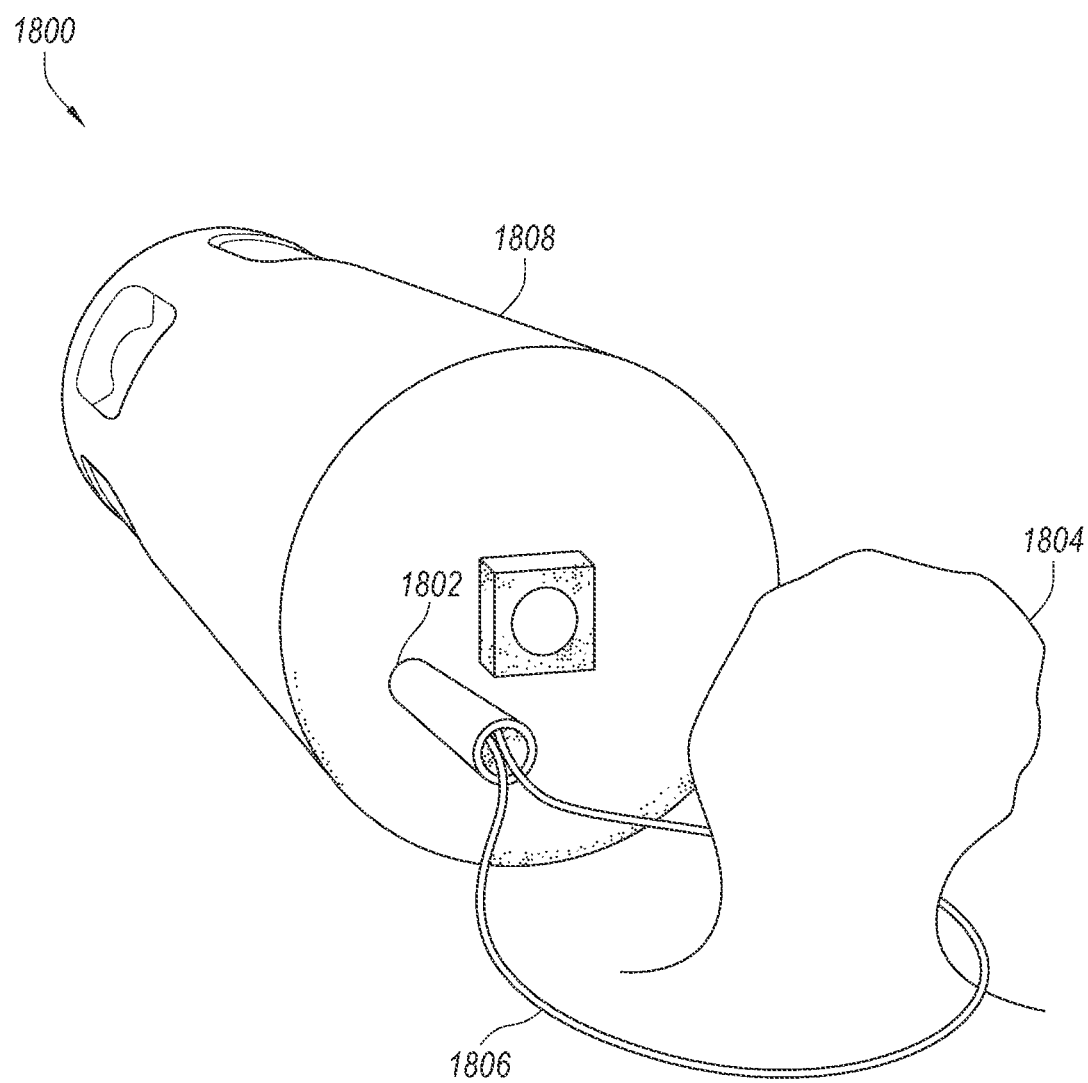
FIG. 18A is a perspective view of an ingestible device with an intervention component capable of excising a polyp that protrudes from the tissue.

FIG. 18A is a perspective view of an ingestible device 1800 with an intervention component 1802 capable of excising a polyp 1804 that protrudes from the tissue. Such intervention components may be referred to as "polypectomy mechanisms," "polypectomy implements," or "polypectomy tools." As shown in FIG. 18A, the intervention component 1802 may include a loop of wire 1806 that can be placed around the polyp 1804 similar to a lasso and then drawn closed, thereby shearing the polyp 1804 from the tissue at its base. The polyp 1804 may be brought within the capsule 1808 for transport out of the living body.

Wire-based resection of samples may be facilitated by other intervention components. For example, the polyp 1804 may be targeted with energy by another intervention component (e.g., an ablation element that targets the polyp 1804 with RF waves, microwaves, etc.). As another example, the polyp 1804 may be severed by a cutting mechanism (also referred to as a "cutting implement"). As another example, the ingestible device 1800 may include a grasping mechanism (e.g., a manipulator arm) able to manipulate and/or explore the polyp 1804.

Other embodiments may include rotational excision features intended to shear away material that is not substantially protruding from the surrounding tissue. One example of a rotational excision feature is a rotatable cutting element that comprises a shaft with a cutting flute. Rotational excision features may feature cutting surface(s) with high rake angles to facilitate peeling away of severed material. The relief angle behind the cutting surface(s) may serve to lower friction and enhance cutting efficiency. Severed material may be entrapped or retracted into the capsule for further study outside of the living body, or the severed material may simply be allowed to exit the living body via natural peristalsis.

FIG. 18B is a perspective of another ingestible device 1850 with an intervention component 1852 capable of excising a polyp 1854. Like the intervention component 1802 of FIG. 18A, the intervention component 1852 may include a loop of wire 1856 that can be deployed from, and then drawn into, a hollow structural body 1858. In some embodiments, the hollow structural body 1858 is extended into the surrounding environment through the capsule 1860 and then held while the polyp 1854 is excised. In other embodiments, the hollow structural body 1858 is extended into the surrounding environment through the capsule 1860 and then retracted into the capsule 1860 in a single motion. Both of these approaches may allow for multiple samples (e.g., of the sample structure or different structures) to be obtained as the ingestible pill 1850 traverses the living body. Actuation of the intervention component 1852 can be accomplished using MEMS devices, mechanical springs, electric motors, solenoids, and the like.

As shown in FIG. 18B, the loop of wire 1856 can be deployed to excise at least a portion of the polyp 1854 through shearing action as the loop of wire 1856 is drawn to a close to form a channel. The loop of wire 1856 may comprise braided stainless steel, a chain link of MEMS devices with cutting elements and/or shearing elements, monofilament polymer, braided polymer, or another flexible material having high tensile strength. For example, a chain link of MEMS devices may be desirable if high linear force would be useful for retraction.

Figure 19:
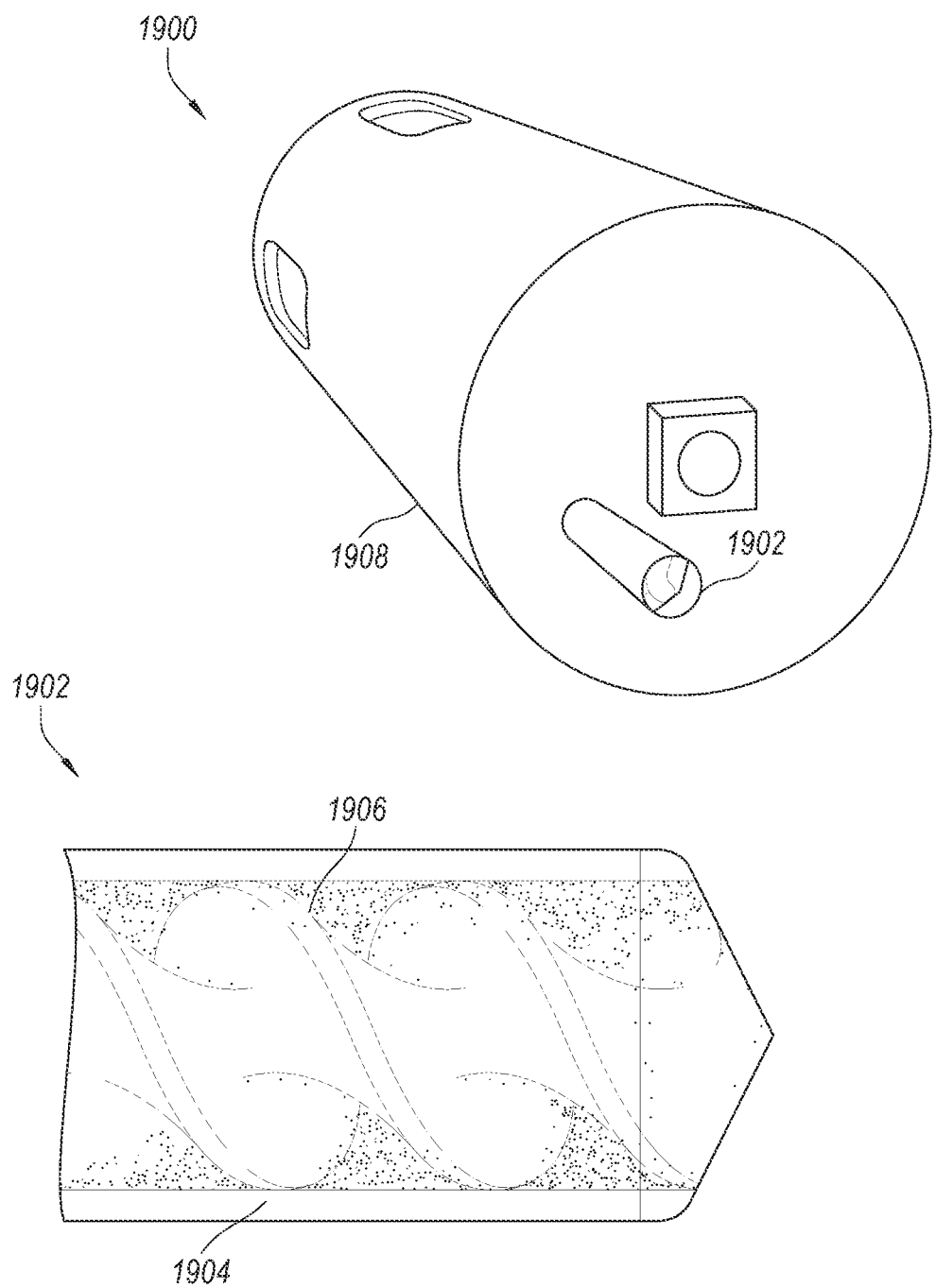
FIG. 19 is a perspective view of an ingestible device with an intervention component that has one or more sharpened edges for cutting.

FIG. 19 is a perspective view of an ingestible device 1900 with an intervention component 1902 that has one or more sharpened edges for cutting. Such intervention components may be referred to as "cutting mechanisms" or "cutting implements." In FIG. 19, the intervention component 1902 is a rotational excision feature that comprises a shaft 1904 with a cutting flute 1906 for obtaining samples. The cutting flute 1906 may have a high radial rake angle in addition to a high radial relief angle to promote slicing and/or peeling of the sample from its original location. A driving mechanism(s) responsible for rotating the shaft 1904 may be located inside the capsule 1908.

Samples may be carried into the capsule 1908 by an Archimedes screw. Alternatively, the ingestible device 1900 may include another intervention component that is configured to capture the samples once separated by the cutting flute 1906. For example, the ingestible device 1900 may include a grasping mechanism able to grasp samples or a mechanical jaw able to encapsulate samples. Samples that have been carried into the capsule 1908 may be further macerated in some embodiments. For example, material (e.g., tissue) captured within the cutting flute 1906 may be provided to shearing elements located inside the capsule 1908.

As discussed above, the intervention component 1902 may be exposed to the surrounding environment by advancing it through an aperture in the capsule 1908 that is initially occluded by a rigid barrier, or the intervention component 1902 may be exposed to the surrounding environment by advancing it through a flexible barrier having an opening defined therein. Alternatively, the intervention component 1902 may be exposed to the surrounding environment by advancing it through a hemispherical housing that comprises shape memory alloy and serves to encapsulate the sample after cutting action is complete.

Figure 20:
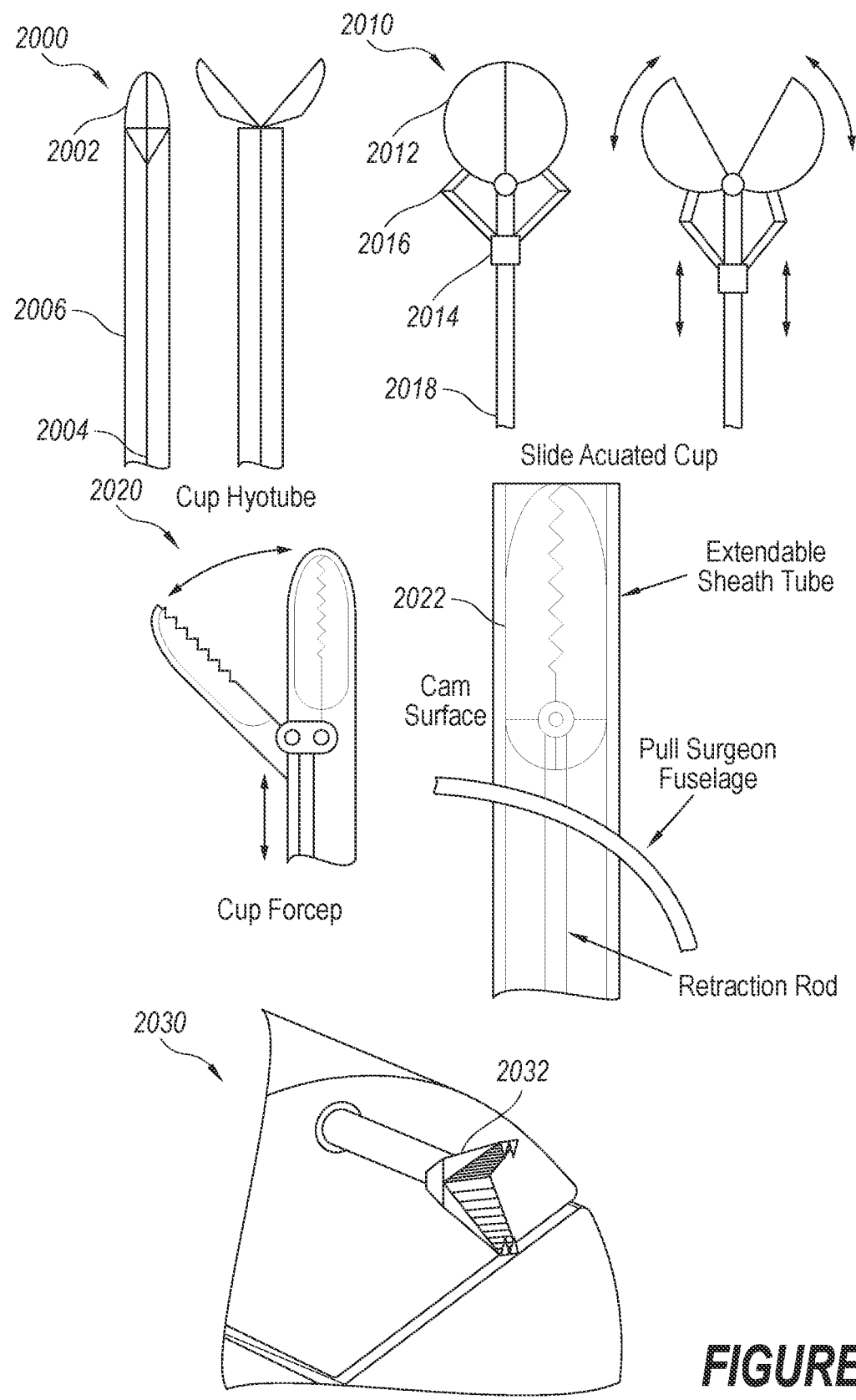
FIG. 20 includes four examples of intervention components that are able to grasp structures in the living body.

FIG. 20 includes four examples of intervention components 2000, 2010, 2020, 2030 that are able to grasp structures in the living body. Such intervention components may be referred to as "grasping mechanisms" or "grasping implements" or "grasping tools."

The first intervention component 2000 includes a pair of mechanical jaws 2002 connected to a structural body 2004 that can be pistoned within a hollow structural body 2006. When the pair of mechanical jaws 2002 is extended away from the opening of the hollow structural body 2006, the pair of mechanical jaws 2002 may naturally open. However, when the pair of mechanical jaws 2002 is drawn into the opening of the hollow structural body 2006, the pair of mechanical jaws 2002 may close (e.g., due to pressure applied by the edge of the hollow structural body 2006).

The second intervention component 2010 includes a pair of mechanical jaws 2012 that can be actuated by moving a throat piece 2014 that is connected to supportive arms 2016 along a structural body 2018. When the throat piece 2014 is moved away from the pair of mechanical jaws 2012 along the structural body 2018, tension is applied to the supportive arms 2016, which results in the supportive arms 2016 pulling the pair of mechanical jaws 2012 into an open state. When the throat piece 2014 is moved upward along the structural body 2018, the supportive arms 2016 will flex, resulting in removal of the tension. Removing the tension may cause the pair of mechanical jaws 2012 to return to a closed state.

In some embodiments, both of the mechanical jaws are actuable. Thus, each mechanical jaw may be able to move between a first position (also referred to as an "open position") and a second position (also referred to as a "closed position"). However, in other embodiments, only one of the mechanical jaws is actuable. In such embodiments, one mechanical jaw will remain in the closed position while the other mechanical jaw moves between the open and closed positions. The third intervention component 2020 includes a pair of mechanical jaws 2022, though only one of the mechanical jaws is actuable between the open and closed states.

Some grasping mechanisms are designed simply to grasp structures in the living body. The fourth intervention component 2030 is an example of such a grasping mechanism. In particular, the fourth intervention component 2030 includes a pair of mechanical jaws 2032 that may be referred to as "rat tooth jaws" or "alligator jaws." Other grasping mechanisms are designed to cut structures in the living body. For example, at least one of a pair of mechanical jaws may have a sharpened edge for cutting. These mechanical jaws (also referred to as "cutting jaws" or "shearing jaws") may be closed around a structure so as to shear it off, or these mechanical jaws may take successive "bites" until sufficient material has been removed from a structure. A single "bite" of material may be brought back into the ingestible device (e.g., and stored in a storage bay as discussed with reference to FIG. 17) for further analysis outside of the living body. Sharpened edges may be useful for ensuring that samples can be obtained without applying significant torque to the structures from which those samples are taken.

A pair of mechanical jaws may be designed to be structurally complementary to one another to enable efficient capture and retainment of samples. For example, as shown in FIG. 20, some mechanical jaws may have a roughly linear profile while other mechanical jaws may have profiles that resemble saw waves, sinusoidal waves, square waves, etc. When a pair of mechanical jaws are in the closed position, a cavity may be formed in which a sample can be held. The cavity may be partially or fully enclosed by the pair of mechanical jaws. For example, a pair of mechanical jaws may be designed to isolate the sample from the surrounding fluids in order to minimize the likelihood of contamination.

Figure 21:
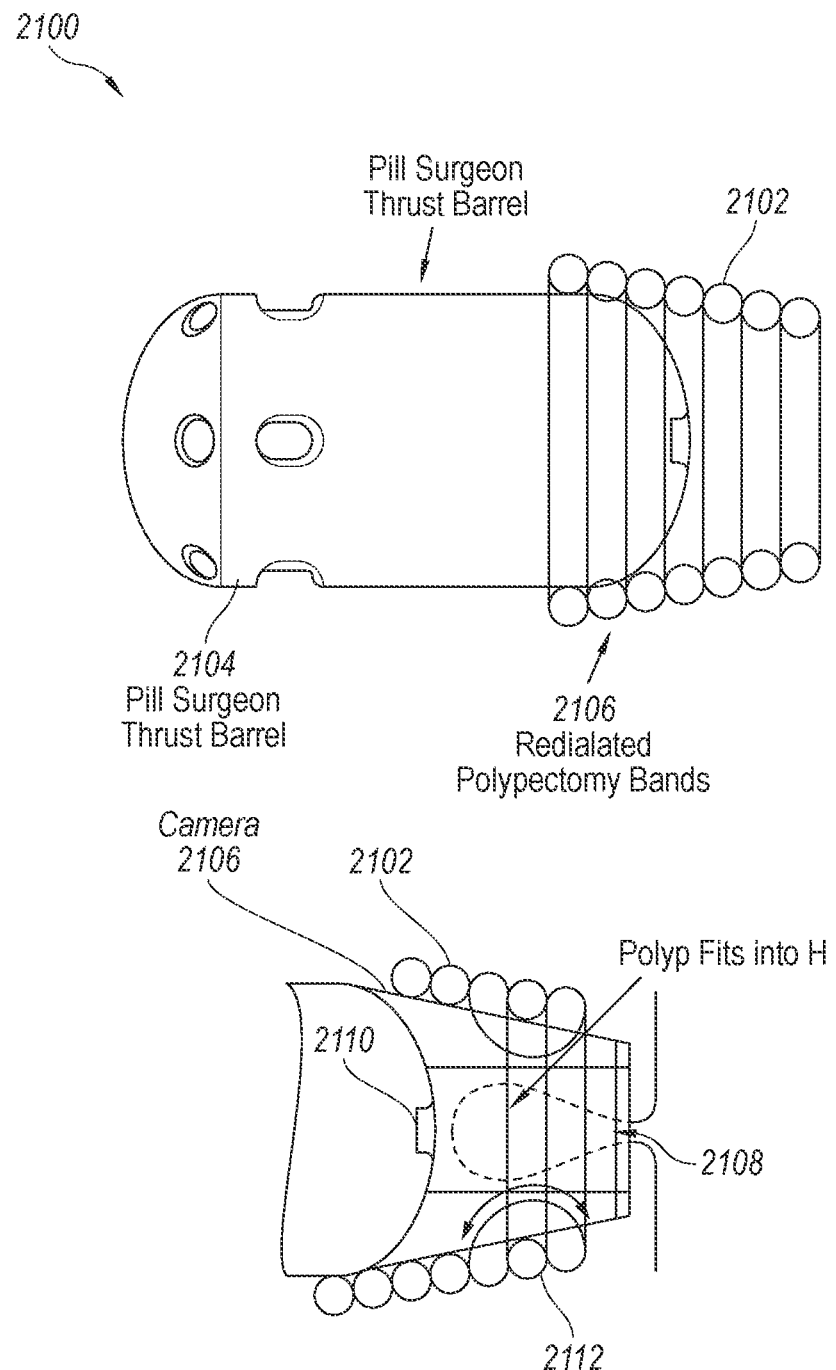
FIG. 21 includes side views of an ingestible device that has one or more elastic bands secured around its proximal end.

FIG. 21 includes side views of an ingestible device 2100 that has one or more elastic bands 2102 secured around its proximal end. These elastic band(s) 2102 may be deployed around a structure (e.g., a polyp) in order to reduce or eliminate circulation for eventual sloughing off. The elastic band(s) 2102 may initially be secured around a tapered section 2106 of the capsule 2104. The tapered section 2106 may have a hollow core 2108 through which light can be collected for imaging by a camera 2110. As shown in FIG. 21, a pair of escapement arms 2112 can be configured to rotate to release an elastic band around a structure of interest and then position the next elastic band in preparation for release. As elastic bands are released from the tapered section 2106 of the capsule 2104, the remaining elastic bands may roll forward due to the taper.

Figure 22:
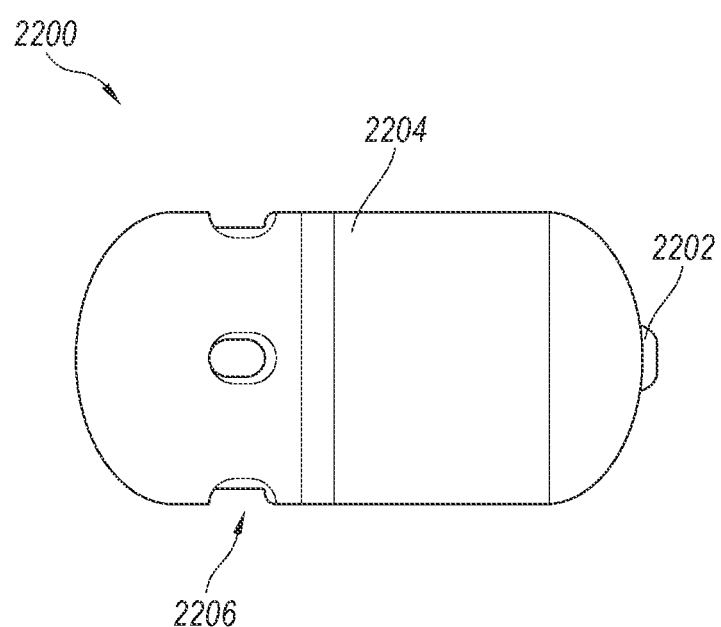
FIG. 22 is a perspective view of an ingestible device that includes an intervention component having a blunt form that can be used to depress tissue so as to temporarily displace circulating blood.

FIG. 22 is a perspective view of an ingestible device 2200 that includes an intervention component 2202 having a blunt form that can be used to depress tissue so as to temporarily displace circulating blood. In FIG. 22, the intervention component 2202 is representative of an extended nose section that protrudes from the proximal end of the capsule 2204. The intervention component 2202 may extend, either partially or entirely, around the camera. Thus, the intervention component 2202 may have an annular form that completely surrounds the camera. The thickness of the intervention component 2202 may be less than 0.5 millimeters (mm), 1 mm, or 2 mm. The intervention component 2202 may comprise polycarbonate or another rigid, biocompatible material.

Initially, the ingestible device 2200 can be aligned with a structure that is to be depressed. The structure may be, for example, the stomach lining or intestine lining (also referred to as the "epithelium"). Then, the ingestible device 2200 can employ the propulsor(s) 2206 located at the distal end to thrust the intervention component 2202 into the structure. Thus, blunt depression may be achieved through the use of the propulsion system of the ingestible device 2200. Alternatively, blunt depression may be achieved through mechanical deployment of the intervention component 2202 relative to the capsule 2204. For example, the intervention component 2202 may be mechanically actuated between a retracted state and an extended state to apply pressure to the structure. Mechanical deployment may be accomplished via solenoid action, rack and pinion action (e.g., an electric motor with corresponding gears), spring loading, pneumatic loading, hydraulic loading, etc.

Vascularity and/or health may be inferred based on the speed at which blood is replaced upon removal of the intervention component 2202 from the structure. As an example, cancerous lesions tend to have high vascularity and blood refill rates. Thus, the ingestible device 2200 may cause the camera to capture a series of images immediately after the intervention component 2202 has been removed from the structure and then transmit the series of images to a receiver (e.g., in a controller) for further analysis.

Figure 23:
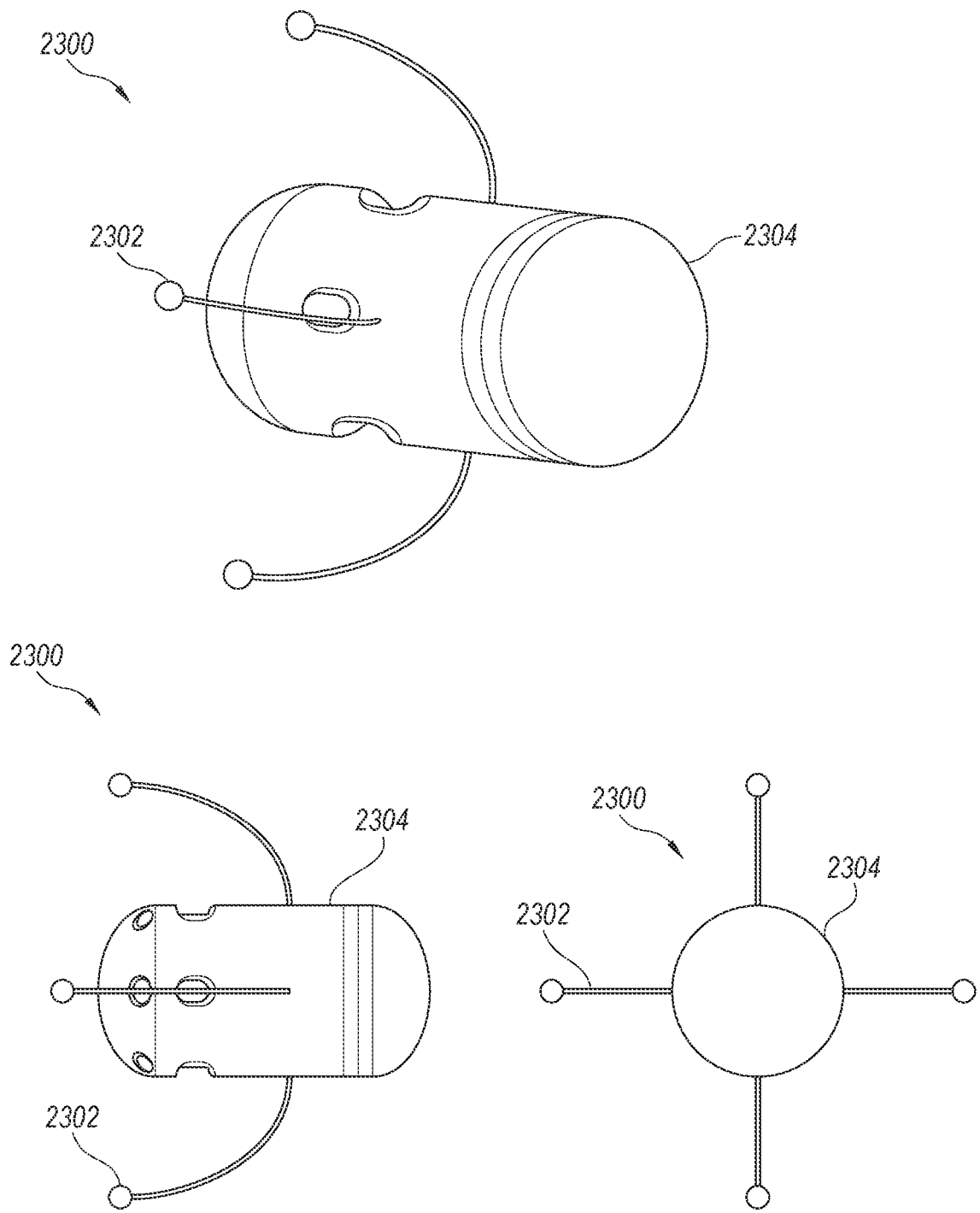
FIG. 23 includes perspective, side, and end views of an ingestible device that includes a plurality of anchoring members that can be used for stabilization.

FIG. 23 includes perspective, side, and end views of an ingestible device 2300 that includes a plurality of anchoring members 2302 that can be used for stabilization. In FIG. 23, the ingestible device 2300 includes four anchoring members 2302 spaced circumferentially about the capsule 2304 in an even spacing. Other embodiments of the ingestible device 2300 could include greater or fewer than four anchoring members 2302. While the anchoring members 2302 are shown as extending from the proximal end of the capsule 2304 toward the distal end of the capsule 2304, the anchoring members 2302 could be anchored along any part of the capsule.

The anchoring members 2302 may be in the form of hoops or wires. In embodiments where the anchoring members 2302 are wires, the end of each wire may be rendered blunt. For example, heat may be successively applied to the end of each wire by a laser welder to form a spherical element whose cross-sectional area is significantly larger than the cross-sectional area of the wire. Such an approach ensures the anchoring members 2302 can engage tissue in an atraumatic manner.

The anchoring members 2302 can engage tissue so as to mechanically lock the ingestible device 2300 in place. Such an approach may be useful for performing detailed diagnostics, providing apposition force for intervention components that must be thrust against target anatomy with more force than the propulsion system is capable of providing, or eliminating electrical drain associated with hover-in-place commands. Thus, the anchoring members 2302 may be used to provide leverage (e.g., when obtaining a sample with a biopsy mechanism) instead of, or in addition to, the propulsion system of the ingestible device 2300. The anchoring members 2302 may be actuated via shape memory alloy, rack-and-pinion style extensions (e.g., driven by electric motor and corresponding gears), or elastically loaded elements that take a different shape when extended from a holding cavity, rail, etc.

Figure 24A:
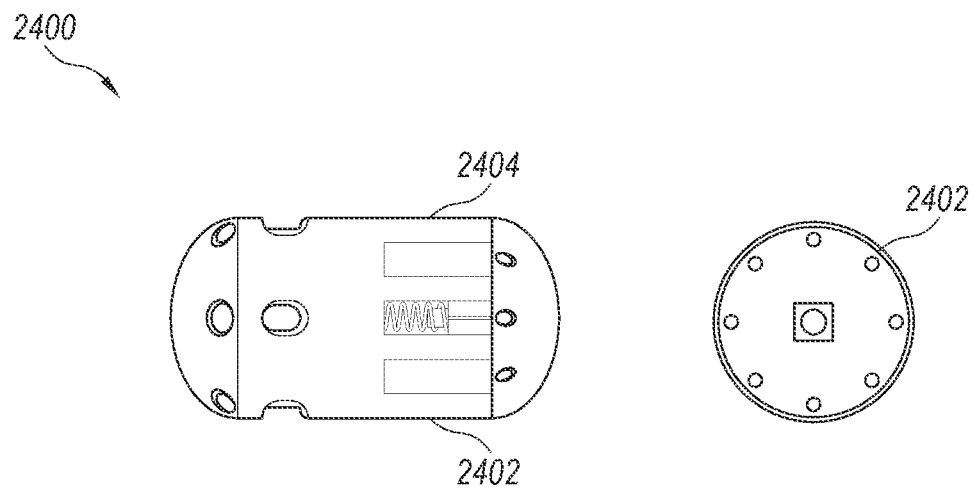
FIG. 24A includes side and end views of an ingestible device that includes a series of intervention components having material stored therein.

FIG. 24A includes side and end views of an ingestible device 2400 that includes a series of intervention components 2402 having material stored therein. These intervention components 2402 can be used to deliver the corresponding materials to target anatomy in the living body, and thus may be referred to as "delivery mechanisms" or "delivery implements." One example of a delivery mechanism is a spring-loaded syringe loaded with material that can be injected into a structure. Another example of a delivery mechanism is a compartment loaded with material that can be released into the environment surrounding the ingestible device 2400.

Examples of materials include medications, cauterization agents, radiation enhancement agents, and inks. For example, a delivery mechanism may include a therapeutic medicine, drug, natural hormone, or bioidentical hormone that can be released for treatment purposes. As another example, a delivery mechanism may include a cauterization agent, such as silver nitrate, to reduce bleeding from a wound inside the living body. As another example, a delivery mechanism may include a radiation enhancement agent that is released to improve contrast and/or quality of images captured during a radiation-based imaging procedure. As another example, a delivery mechanism may include an ink that can be used to permanently or temporarily mark a location within the living body (e.g., that may be targeted in subsequent procedures).

Figure 24B:
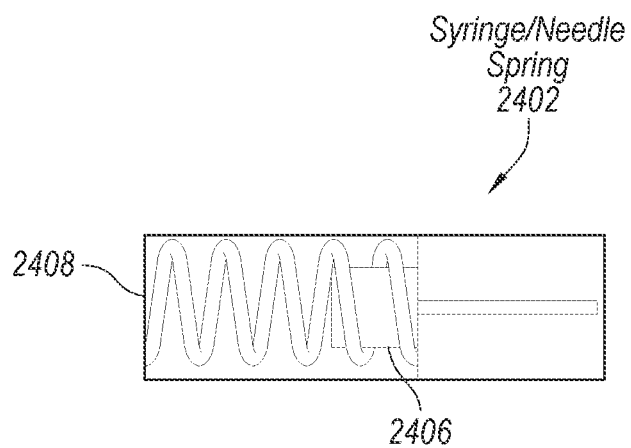
FIG. 24B illustrates how an intervention component having material stored therein can be actuated by a spring.

A delivery mechanism may be capable of being advanced into a structure to inject the material stored therein. FIG. 24B illustrates how an intervention component 2402 having material 2406 stored therein can be actuated by a spring 2408. Other embodiments of the intervention component 2402 may be actuated by MEMS devices, hydraulic means, pneumatic means, or chemical means. In some embodiments, the intervention component 2402 is configured to piston within a hollow structural body having a cavity therein that is exposed to the surrounding environment through the capsule 2404. In such embodiments, fluid flow into the capsule 2404 can be inhibited by sealing each tube in accordance with the process discussed above with reference to FIGS. 7A-B. In other embodiments, the intervention component 2402 is configured to extend through an aperture in the capsule 2404. For example, each intervention component 2402 may be able to extend through an aperture that has a flexible barrier which inhibits the flow of fluid into the capsule 2404.

Figure 25:
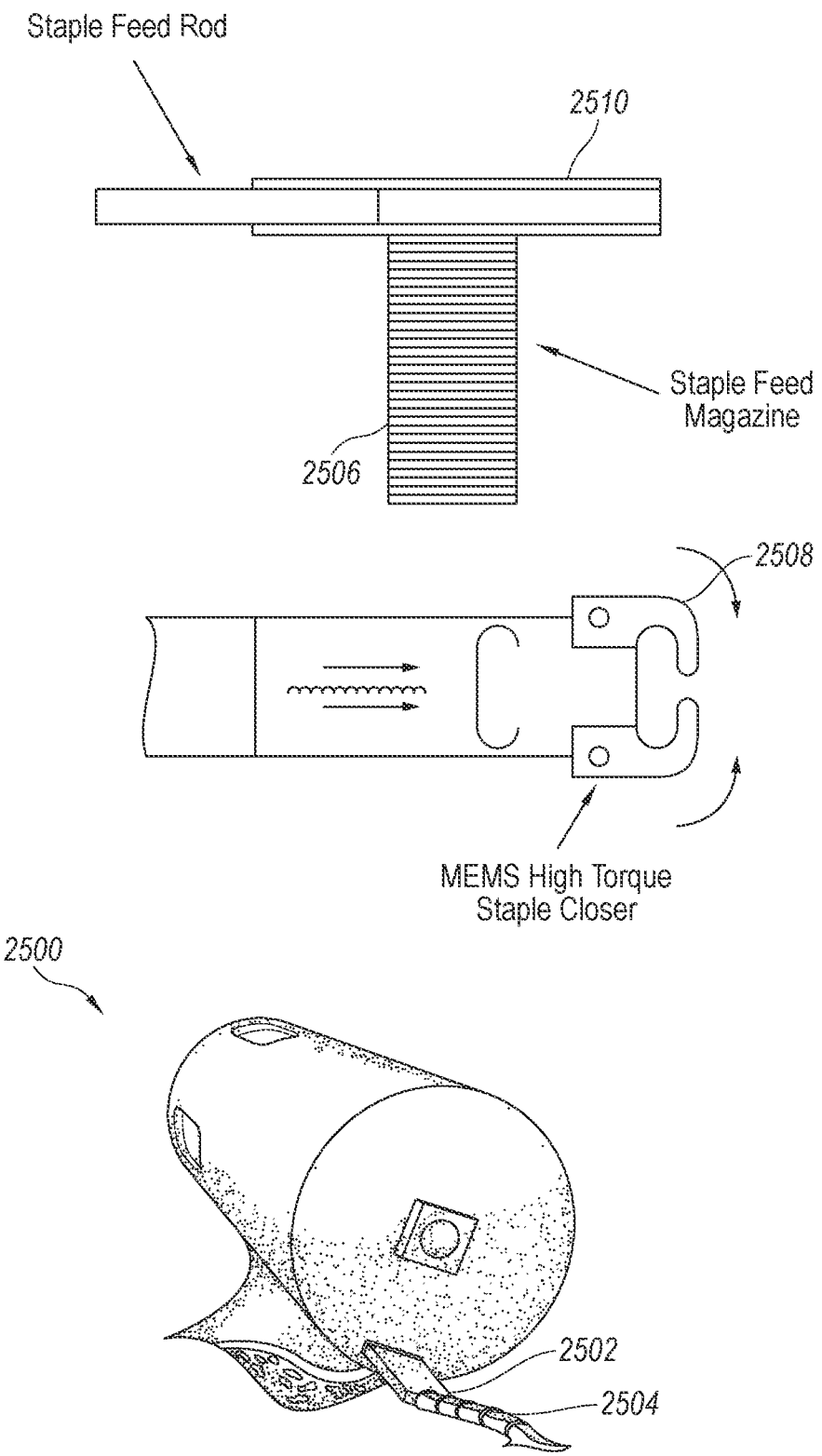
FIG. 25 includes a perspective view of an ingestible device that includes an intervention component that is capable of storing and then deploying surgical staples.

FIG. 25 includes a perspective view of an ingestible device 2500 that includes an intervention component 2502 that is capable of storing and then deploying surgical staples 2504 (or simply "staples"). Staples may be employed to close wounds resulting from open bleeding, polypectomies, biopsies, etc. Staples may be closed by a high-torque, slow-action mechanism 2508, such as a MEMS device, included in the intervention component 2502.

In some embodiments the staples comprise metal alloy, while in other embodiments the staples comprise a bioabsorbable material (also referred to as a "bioresorbable material"). The terms "bioabsorbable materials" and "bioresorbable materials," as used herein, refer to materials that, upon placement within a living body, will begin to dissolve and slowly be replaced by tissue. Examples of bioabsorbable material include tricalcium phosphate and polylactic-polyglycolic acid copolymers. Bioabsorbable materials may be desirable if the wound is expedited to heal over time, thereby rendering the staples unnecessary.

In FIG. 25, the intervention component 2502 includes a magazine 2506 of staples that can be fed to a high-torque, slow-action mechanism 2508 via a feeding mechanism 2510, such as a feeding rod. However, wounds could be closed in other ways. For example, embodiments of the ingestible device 2500 may be able to apply bioabsorbable adhesives (e.g., polyethylene glycol-based (PEG-based) hydrogels) or biocompatible adhesives (e.g., polymethyl methacrylate (PMMA)). As another example, embodiments of the ingestible device 2500 may be able to apply bioabsorbable sutures or bioabsorbable stents.

Figure 26:
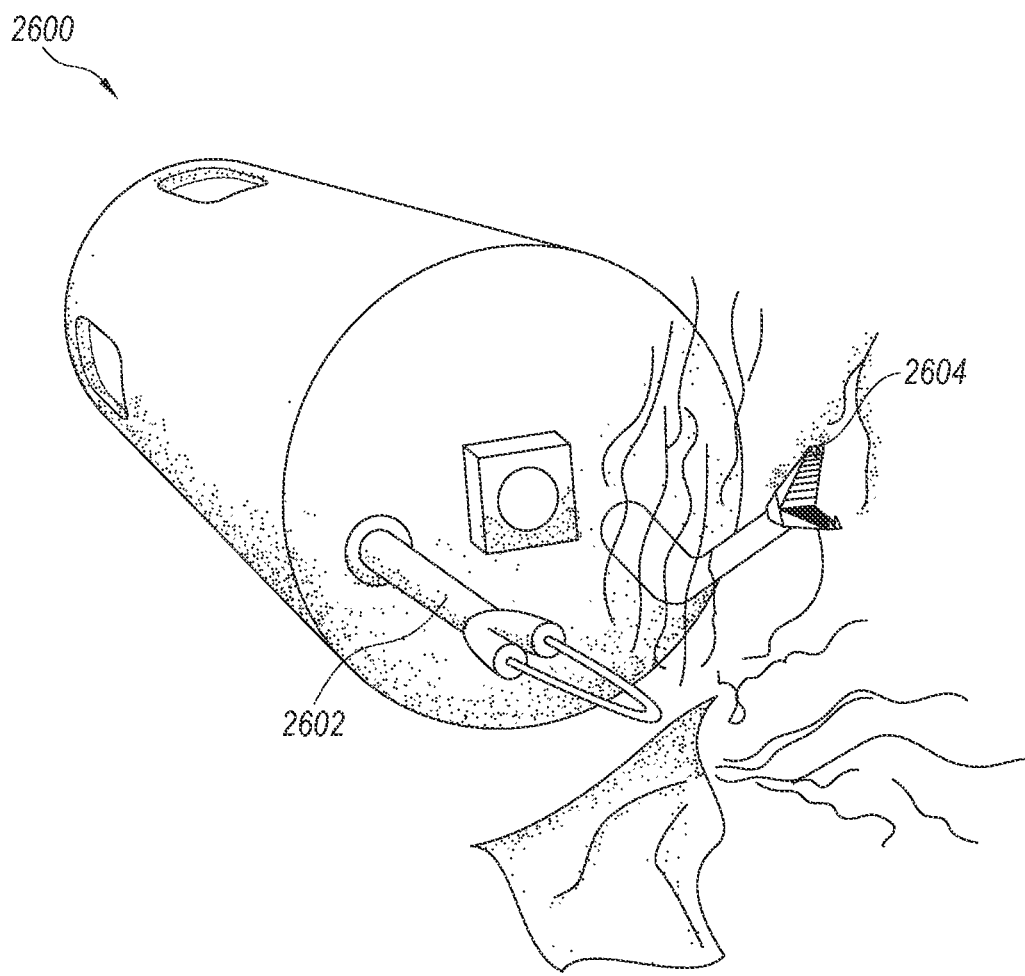
FIG. 26 includes a perspective view of an ingestible device that includes an intervention component that is capable of cauterizing tissue inside a living body.

FIG. 26 includes a perspective view of an ingestible device 2600 that includes an intervention component 2602 that is capable of cauterizing tissue inside a living body. Such intervention components 2602 may be referred to as "cauterization mechanisms" or "cauterization implements." Cauterization may be employed to close wounds resulting from open bleeding, polypectomies, biopsies, etc. As such, cauterization mechanisms are often accompanied by biopsy mechanisms, grasping mechanisms, etc. In FIG. 26, for example, the ingestible device 2600 includes a first intervention component 2602 capable of cauterizing tissue and a second intervention component 2604 capable of grasping the tissue (and surrounding structures, if necessary).

In some embodiments, the intervention component 2602 includes a resistive heating element that applies heat to the tissue through conduction. In other embodiments, the intervention component 2602 includes an ablation element that applies heat by directly targeting the tissue with RF waves, microwaves, etc. Thus, heat may be transferred to the tissue via conduction, convection, or radiation.

Ingestible devices may include other intervention components in addition to, or instead of, those discussed with reference to FIGS. 13-26. For example, an ingestible device may include a grasping element that comprises a shaft with barbs along the distal end (e.g., along the surface of a spherical or tapered element). In such embodiments, the ingestible device can extend the grasping element so as to penetrate a structure of interest. Then, the ingestible device may partially retract the intervention component such that at least a portion of the structure is dislodged as a sample. In some embodiments the intervention component is retracted into the ingestible device to permit subsequent analysis of the sample, while in other embodiments the intervention component is detached from the ingestible device so as to release the sample into the living body.

Communication Environment

Figure 27:
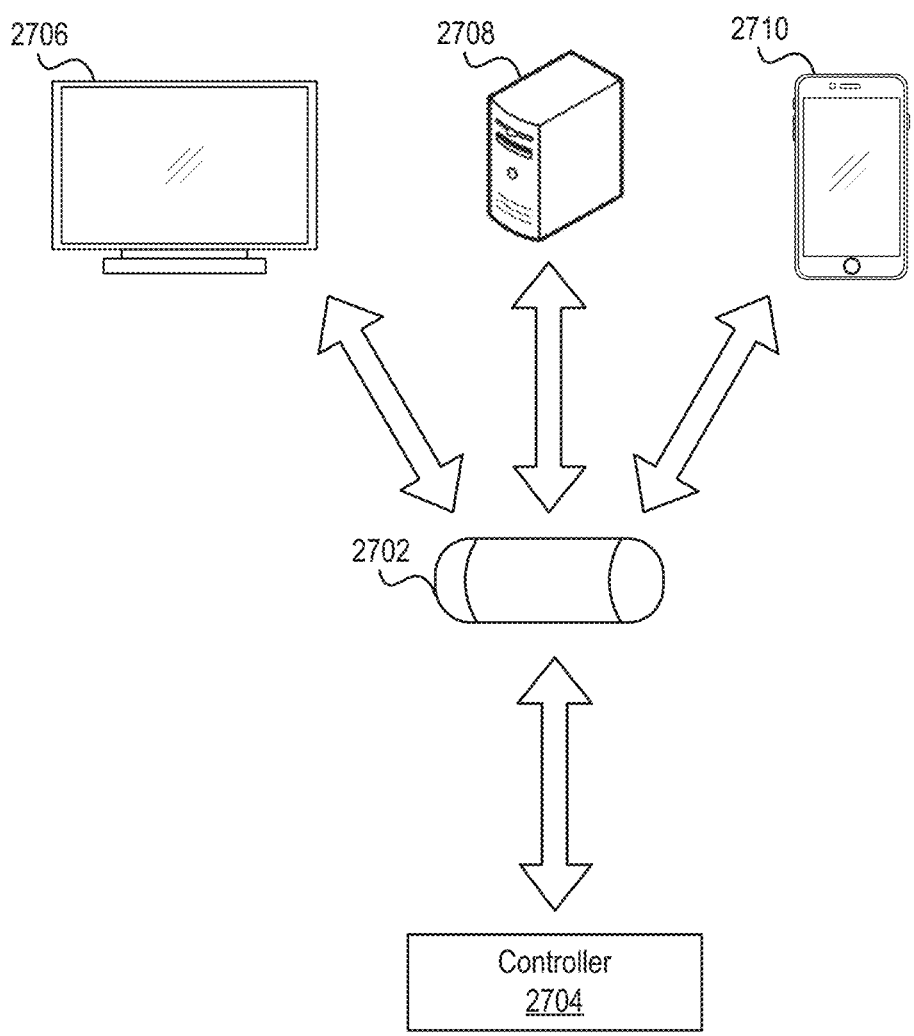
FIG. 27 depicts an example of a communication environment that includes a propulsive ingestible device that is communicatively coupled to a controller.

FIG. 27 depicts an example of a communication environment 2700 that includes an ingestible device 2702 that is communicatively coupled to a controller 2704. An operator can control the ingestible device 2702 using the controller 2704. Moreover, the ingestible device 2702 can be configured to transmit data (e.g., image data or biometric data) to one or more electronic devices. Examples of electronic devices include monitors 2706, computer servers 2708, and mobile phones 2710. The ingestible device 2702, controller 2704, and electronic device(s) may collectively be referred to as the "networked devices."

In some embodiments, the networked devices are connected to one another via point-to-point wireless connections as shown in FIG. 27. For example, the ingestible device 2702 may be communicatively coupled to the controller 2704 via Bluetooth®, Near Field Communication (NFC), Wi-Fi® Direct (also referred to as "Wi-Fi P2P"), Zigbee®, another commercial point-to-point protocol, or a proprietary point-to-point protocol. In other embodiments, the networked devices are connected to one another via networks, such as personal area networks (PANs), local area networks (LANs), wide area networks (WANs), metropolitan area networks (MANs), cellular networks, or the Internet. For example, the ingestible device 2702 may be communicatively coupled to a monitor 2706 and a computer server 2708 via separate LoRa® communication channels.

The connections established between the networked devices may be bidirectional or unidirectional. For example, the controller 2704 may be permitted to transmit data to the ingestible device 2702 even though the ingestible device 2702 may be unable to transmit data to the controller 2704. Similarly, the ingestible device 2702 may be permitted to transmit data to the electronic device(s) even though the electronic device(s) may be unable to transmit data to the ingestible device 2702.

Embodiments of the communication environment 2700 may include some or all of the networked devices. For example, some embodiments of the communication environment 2700 include an ingestible device 2702 and a single device (e.g., a mobile phone, tablet computer, or mobile workstation) that serves as the controller and the electronic device on which image data is reviewed. As another example, some embodiments of the communication environment 2700 include an ingestible device 2702 and a computer server 2708 on which the image data is stored for subsequent review. In such embodiments, because the image data will be reviewed at some later point in time, the communication environment 2700 need not include a controller 2704. As another example, some embodiments of the communication environment 2700 include a dedicated input device without display capabilities that serves as the controller 2704 and an electronic device, such as a tablet computer or a mobile phone, on which image data is reviewed. In such embodiments, the dedicated input device may be communicatively coupled to the ingestible device and/or the electronic device.

Since the ingestible device 2702 can operate in vivo, the close proximity to fluids, tissue, and the like may affect the electromagnetic operating characteristics of the antenna. To address this, the antenna may be designed and/or selected to minimize the effects of nearby materials having relative dielectric constants that are significantly different from free space. As an example, an embodiment could use a small loop antenna with one or more turns, which primarily interacts with magnetic field components in the near field, and is therefore less strongly affected by the proximity of high-dielectric materials. Alternatively, the antenna may be designed and/or selected to compensate for the effect of the fluid(s) inside the living body. As an example, an embodiment could use a straight, bent, curved, or meandered antenna (e.g., monopole antenna) where the effective electrical antenna length is between one-eighth and one-third of the transceiver operating wavelength when the ingestible device 2702 is surrounded by fluid or anatomy of the living body. For instance, an embodiment could use a monopole or "whip" antenna that is significantly shorter than a free-space quarter wavelength. While this antenna would not be tuned optimally in air, proximity to the high-dielectric fluid(s) may cause the antenna to behave electrically as if it were significantly longer and tuned properly to the frequency of interest. Such an approach also has the benefit of allowing the use of a significantly smaller antenna than would be optimal for operation in dry air. The mechanical structure of the antenna may be designed to conform to the enclosure of the ingestible device 2702.

The antenna and transceiver circuitry may be designed such that a single antenna is used for both transmitting and receiving data. Alternatively, multiple antennas may be used. For example, different antennas may offer superior performance in certain orientations or fluid conditions, and the performance of each antenna may be monitored during operation in order to select the antenna with the highest performance at any given point in time. In embodiments that use wireless power transmission, the ingestible device 2702 may be configured to use a single antenna for both power and data transmission to eliminate the need for an additional antenna. Alternatively, different antennas or electromagnetically coupled structures may be used for power and data transmission, allowing each to be optimized for its respective task.

To allow multiple ingestible devices to operate within close proximity (e.g., multiple patients undergoing treatment in the same room or building), the communication channels discussed above may be established using a pairing feature. Pairing features may be employed to ensure that each ingestible device communicates with a single controller. To accomplish this, each ingestible device may be assigned a unique identification number during manufacturing. When a communication channel is established by an ingestible device, the ingestible device may transmit its identifier to establish whether the communication channel was established with the appropriate controller. Additionally or alternatively, the ingestible device may append the identifier (or a shortened/amended identifier) as a label to data packets to designate the appropriate controller. Accordingly, each controller may assume that data packets without the correct identifier are meant to be received by another controller and thus can be ignored. As part of this process, the ingestible device and corresponding controller may elect to switch to a different communication channel or frequency to avoid having to share time and bandwidth with other pairs of ingestible devices and controllers. The ingestible device and corresponding controller may elect to change communication frequency as needed during operation to avoid competing with interfering devices, a strategy known as "frequency hopping."

Processing System

Figure 28:
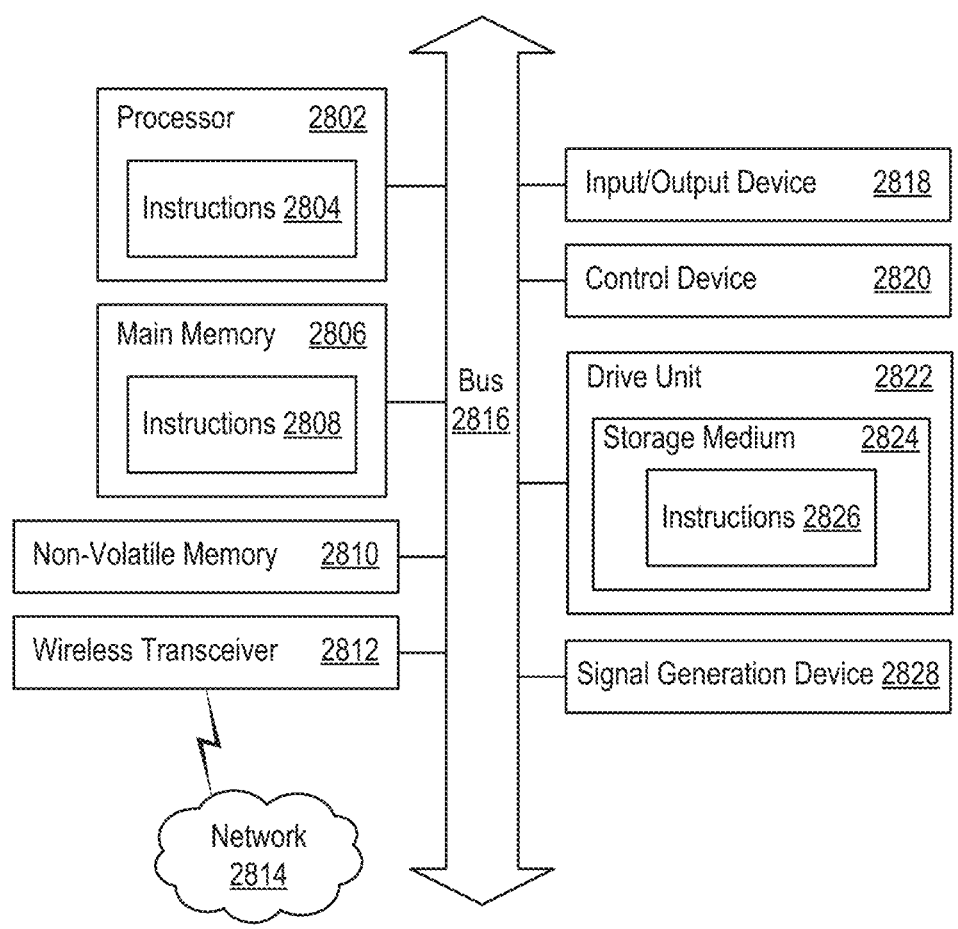
FIG. 28 is a block diagram illustrating an example of a processing system in which at least some operations described herein can be implemented.

FIG. 28 is a block diagram illustrating an example of a processing system 2800 in which at least some operations described herein can be implemented. Components of the processing system 2800 may be hosted on an ingestible device (e.g., ingestible device 100 of FIG. 1).

The processing system 2800 may include a central processing unit ("processor") 2802, main memory 2806, non-volatile memory 2810, wireless transceiver 2812, input/output device 2818, control device 2820, drive unit 2822 including a storage medium 2824, and signal generation device 2828 that are communicatively connected to a bus 2816. The bus 2816 is illustrated as an abstraction that represents one or more physical buses and/or point-to-point connections that are connected by appropriate bridges, adapters, or controllers. The bus 2816, therefore, can include a system bus, Peripheral Component Interconnect (PCI) bus, PCI-Express bus, HyperTransport bus, Industry Standard Architecture (ISA) bus, Small Computer System Interface (SCSI) bus, Universal Serial Bus (USB), Inter-Integrated Circuit (I²C) bus, or bus compliant with Institute of Electrical and Electronics Engineers (IEEE) Standard 1394.

The processing system 2800 may share a similar computer processor architecture as that of a desktop computer, tablet computer, mobile phone, video game console, wearable electronic device (e.g., a watch or fitness tracker), network-connected ("smart") device (e.g., a television or home assistant device), augmented or virtual reality system (e.g., a head-mounted display), or another electronic device capable of executing a set of instructions (sequential or otherwise) that specify action(s) to be taken by the processing system 2800.

While the main memory 2806, non-volatile memory 2810, and storage medium 2824 are shown to be a single medium, the terms "storage medium" and "machine-readable medium" should be taken to include a single medium or multiple media that stores one or more sets of instructions 2826. The terms "storage medium" and "machine-readable medium" should also be taken to include any medium that is capable of storing, encoding, or carrying a set of instructions for execution by the processing system 2800.

In general, the routines executed to implement the embodiments of the disclosure may be implemented as part of an operating system or a specific application, component, program, object, module, or sequence of instructions (collectively referred to as "computer programs"). The computer programs typically comprise instructions (e.g., instructions 2804, 2808, 2826) set at various times in various memories and storage devices in an electronic device. When read and executed by the processor 2802, the instructions cause the processing system 2800 to perform operations to execute various aspects of the present disclosure.

While embodiments have been described in the context of fully functioning electronic devices, those skilled in the art will appreciate that the various embodiments are capable of being distributed as a program product in a variety of forms. The present disclosure applies regardless of the particular type of machine- or computer-readable medium used to actually cause the distribution. Further examples of machine- and computer-readable media include recordable-type media such as volatile and non-volatile memory devices 2810, removable disks, hard disk drives, optical disks (e.g., Compact Disk Read-Only Memory (CD-ROMS) and Digital Versatile Disks (DVDs)), cloud-based storage, and transmission-type media such as digital and analog communication links.

The wireless transceiver 2812 enables the processing system 2800 to mediate data in a network 2814 with an entity that is external to the processing system 2800 through any wireless communication protocol supported by the processing system 2800 and the external entity. The wireless transceiver 2812 can include, for example, an integrated circuit (e.g., enabling communication over Bluetooth or Wi-Fi), network adaptor card, or wireless network interface card.

The techniques introduced here can be implemented using software, firmware, hardware, or a combination of such forms. For example, aspects of the present disclosure may be implemented using special-purpose hardwired (i.e., non-programmable) circuitry in the form of application-specific integrated circuits (ASICs), programmable logic devices (PLDs), field-programmable gate arrays (FPGAs), and the like.

Remarks

The foregoing description of various embodiments has been provided for the purposes of illustration. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes various embodiments, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A device comprising:
   a capsule that has a central axis defined through a cylindrical body that is interconnected between a first end and a second end and comprises a biocompatible material suitable for ingestion by a living body;
   a plurality of propulsors that are spaced about the central axis proximate to the first end of the capsule,
      wherein each propulsor of the plurality of propulsors is situated in a different one of a plurality of channels defined through the capsule, and
      wherein each channel of the plurality of channels has (i) an inlet located in the cylindrical body of the capsule and (ii) an outlet located in the first end of the capsule;
   an intervention tool configured to manipulate a structure in the living body when extended from the capsule through an aperture proximate to the second end of the capsule;
   a plurality of storage bays to store a respective plurality of biopsy samples;
   a rotatable platform within the capsule, wherein the plurality of storage bays are distributed radially on the rotatable platform;
   a sensor configured to generate image data based on energy reflected by the structure;
   an antenna;
   a processor configured to cause transmission of the image data to a receiver located outside the living body via the antenna; and
   a transceiver configured to modulate the image data prior to transmission by the antenna.

2. The device of claim 1, wherein the intervention tool includes a biopsy appendage, and wherein the processor is further configured to:
   receive first input indicative of an instruction to deploy the biopsy appendage to collect a sample from the structure,
   cause the biopsy appendage to extend through the aperture toward the structure, and
   cause the biopsy appendage to retract from the structure through the aperture in the capsule.

3. The device of claim 2, wherein the biopsy appendage is retracted from the structure responsive to the processor receiving second input indicative of an acknowledgement that the biopsy appendage successfully collected the sample.

4. The device of claim 3, wherein the acknowledgement is generated by another sensor that is configured to monitor whether the biopsy appendage includes the sample.

5. The device of claim 3, wherein the acknowledgement is submitted through an electronic device by a person.

6. The device of claim 2, wherein the biopsy appendage comprises a needle having a hollow body with a sharpened tip at a distal end.

7. The device of claim 6, wherein the needle includes a hollow structural body and a barb along an inner surface of the hollow structural body, and wherein the barb is oriented in such a manner to inhibit removal of the sample from the hollow structural body when the sharpened tip is withdrawn from the structure.

8. The device of claim 1, further comprising:
   a barrier configured to inhibit exposure of the intervention tool to the living body while the barrier is in a first position,
      wherein the aperture is completely occluded while the barrier is in the first position; and
      wherein the aperture is at most partially occluded while the barrier is in a second position.

9. The device of claim 8, further comprising a deployment mechanism configured to move the barrier to the first position responsive to the processor determining that the intervention tool has been retracted through the aperture in the capsule.

10. The device of claim 1, further comprising:
    a barrier configured to inhibit exposure of the intervention tool to the living body while the intervention tool is in a first position in which the intervention tool resides entirely inside the capsule; and
    a deployment mechanism configured to move the intervention tool to a second position in which at least part of the intervention tool resides outside the capsule,
       wherein moving the intervention tool from the first position to the second position causes the barrier to be punctured.

11. The device of claim 1, wherein the intervention tool includes a polypectomy tool including a loop of wire, and wherein the processor is further configured to:
    receive input indicative of an instruction to employ the polypectomy tool to gather a sample from the structure,
    cause the loop of wire to extend around a portion of the structure and then retract to shear the portion from the structure, and
    cause the polypectomy tool to retract from the structure while holding the portion of the structure with the loop of wire.

12. The device of claim 1, wherein the intervention tool includes an actuable jaw that has a sharpened edge for cutting.

13. The device of claim 1, wherein the intervention tool includes a shaft with a plurality of barbs arranged along a distal tip, and wherein the processor is further configured to:
    receive input indicative of an instruction to employ the intervention tool to gather a sample from the structure,
    cause the intervention tool to extend toward the structure such that the distal tip penetrates the structure,
    cause the intervention tool to partially retract such that at least a portion of the structure is dislodged as the sample, and
    cause the intervention tool to be detached from the device so as to release the sample into the living body.

14. The device of claim 1,
    wherein the intervention tool includes a grasping mechanism that comprises a plurality of jointed elements that are independently manipulable between a first position and a second position,
    wherein the plurality of jointed elements are spaced apart when each jointed element is in the first position, and
    wherein the plurality of jointed elements are proximate one another when each jointed element is in the second position.

15. The device of claim 1, wherein the intervention tool includes a delivery mechanism having material stored therein, and wherein the processor is further configured to:
    receive input indicative of an instruction to release the material into the living body, and
    cause the delivery mechanism to release at least some of the material stored therein.

16. The device of claim 15, wherein the material is a radiation enhancement agent, a cauterization agent, an ink, or a medication.

17. The device of claim 15, wherein the delivery mechanism includes a needle with a sharpened tip at a distal end through which the material is ejected, and wherein the processor is configured to cause the needle to extend into the structure in the living body so that the at least some of the material is injected into the structure.

18. The device of claim 1, wherein the intervention tool includes a cauterization mechanism configured to apply heat to the structure through conduction, convection, or radiation.

19. The device of claim 1, wherein the intervention tool includes a biopsy appendage to collect the biopsy samples from the structure.

20. A device comprising:
a capsule that has a cylindrical body interconnected between a first end and a second end and that includes a biocompatible material suitable for ingestion by a living body;
a plurality of propulsors that are located proximate to the first end of the capsule,
wherein each propulsor of the plurality of propulsors is located in a different one of a plurality of channels defined through the capsule, and
wherein each channel of the plurality of channels has (i) an inlet located in the cylindrical body of the capsule and (ii) an outlet located in the first end of the capsule;
an intervention tool configured to manipulate a structure in the living body when extended from the capsule;
a sensor configured to generate image data based on energy reflected by the structure;
an antenna;
a processor configured to:
cause, via the antenna, transmission of the image data to a receiver located outside the living body in real time,
receive, via the antenna, first input indicative of a request to employ the intervention tool to manipulate the structure,
generate, in response to receiving the first input, a first instruction that causes the intervention tool to extend toward the structure,
receive, via the antenna, second input indicative of an acknowledgement that the intervention tool manipulated the structure, and
generate, in response to receiving the second input, a second instruction that causes the intervention tool to retract from the structure;
a plurality of storage bays to store a respective plurality of biopsy samples;
a rotatable platform within the capsule, wherein the plurality of storage bays are distributed radially on the rotatable platform; and
a transceiver configured to modulate the image data prior to transmission by the antenna.

21. The device of claim 20, wherein the receiver is included in a controller through which the request and the acknowledgement are input.

22. The device of claim 20, wherein:
the plurality of propulsors are spaced radially about the first end of the capsule,
the intervention tool extends from the second end of the capsule, and
the acknowledgement is representative of an instruction to reposition the device using at least one of the plurality of propulsors.

23. The device of claim 20, wherein the intervention tool includes a biopsy appendage to collect the biopsy samples from the structure.

* * * * *